(12) United States Patent
Sims et al.

(10) Patent No.: US 9,078,702 B1
(45) Date of Patent: Jul. 14, 2015

(54) SPINAL ALIGNMENT CORRECTION SYSTEM AND METHODS OF USE

(71) Applicants: Hewatt McGraw Sims, Tifton, GA (US); Lauren Chase Thornburg, Atlanta, GA (US)

(72) Inventors: Hewatt McGraw Sims, Tifton, GA (US); Lauren Chase Thornburg, Atlanta, GA (US)

(73) Assignee: Amendia, Inc., Marietta, GA (US)

( * ) Notice: Subject to any disclaimer, the term of this patent is extended or adjusted under 35 U.S.C. 154(b) by 0 days.

(21) Appl. No.: 14/220,830

(22) Filed: Mar. 20, 2014

(51) Int. Cl.
*A61B 17/70* (2006.01)
*A61B 17/68* (2006.01)

(52) U.S. Cl.
CPC ......... *A61B 17/7001* (2013.01); *A61B 17/7077* (2013.01); *A61B 2017/681* (2013.01)

(58) Field of Classification Search
CPC ............... A61B 2017/681; A61B 17/7001; A61B 17/7077
USPC .................................................. 606/246, 264
See application file for complete search history.

(56) References Cited

U.S. PATENT DOCUMENTS

| | | | | | |
|---|---|---|---|---|---|
| 2,292,557 | A | * | 8/1942 | Wilson | 470/59 |
| 3,478,639 | A | * | 11/1969 | Gruca | 411/387.1 |
| 3,682,507 | A | * | 8/1972 | Waud | 411/413 |
| 4,189,834 | A | * | 2/1980 | Smith | 433/225 |
| 4,648,388 | A | * | 3/1987 | Steffee | 606/261 |
| 4,673,376 | A | | 6/1987 | Fender | |
| 4,854,311 | A | * | 8/1989 | Steffee | 606/66 |
| 4,959,938 | A | * | 10/1990 | De Caro | 52/410 |
| 5,047,029 | A | * | 9/1991 | Aebi et al. | 606/264 |
| 5,222,954 | A | * | 6/1993 | Baker et al. | 606/264 |
| 5,352,226 | A | * | 10/1994 | Lin | 606/264 |
| 5,782,831 | A | * | 7/1998 | Sherman et al. | 606/86 A |
| 6,248,104 | B1 | * | 6/2001 | Chopin et al. | 606/267 |
| 6,325,583 | B1 | * | 12/2001 | Mattle et al. | 411/413 |
| 6,666,638 | B2 | * | 12/2003 | Craven | 411/413 |
| 7,942,906 | B2 | | 5/2011 | Bishop | |
| 8,066,739 | B2 | | 11/2011 | Jackson | |
| 8,764,803 | B2 | * | 7/2014 | Suddaby | 606/263 |
| 2003/0212400 | A1 | * | 11/2003 | Bloemer et al. | 606/61 |
| 2013/0184759 | A1 | * | 7/2013 | Rinehart et al. | 606/266 |
| 2013/0238036 | A1 | * | 9/2013 | Sinha | 606/304 |
| 2014/0100612 | A1 | * | 4/2014 | Suddaby | 606/273 |

FOREIGN PATENT DOCUMENTS

DE 283489 1/1980

* cited by examiner

*Primary Examiner* — Ellen C Hammond
(74) *Attorney, Agent, or Firm* — David L. King

(57) ABSTRACT

A spinal alignment correction system (1) has a posted lumbar pedicle screw called a MAC Pin (10) which has an elongated shaft (11) and a rod coupler assembly (20) and a cannulated tower (40). The elongated shaft (11) has an inner pedicle screw portion (12) with pedicle threads (12A), an outer second thread portion (14) with second threads (14A) and a transition or intermediate portion (16) disposed between the pedicle screw portion (12) and the second thread portion (14). The cannulated tower (40) when mounted over said elongated shaft (11) abuts said coupler (20) along an outer cam surface and further tightening rotation of the cannulated tower (40) causes outward movement of the elongated shaft (11). The system (1) allows for a controlled alignment correction of malaligned vertebral bodies using a number of methods used to correct a variety of indications.

14 Claims, 35 Drawing Sheets

SPINAL ALIGNMENT CORRECTION SYSTEM AND METHODS OF USE

TECHNICAL FIELD

The present invention is directed to a device for use in correcting various lumbar and thoracic spinal maladies including reduction of Spondylolisthesis and various other corrective procedures and surgical treatment including scoliosis, trauma and other malalignments of the spine.

BACKGROUND OF THE INVENTION

A recently published paper in *The Journal of Bone and Joint Surgery Incorporated* 2014; 96: 53-8 entitled "Evidence—Based Surgical Management of Spondylolisthesis Reduction Or Arthrodesis In Situ" reported "The role of reduction in the operative management of spondylolisthesis is controversial because of its potential complications, including neurologic deficits, prolonged operative time, and loss of reduction." This study reported "The decision to correct high-grade slippage defects by reduction is still a controversial one. In an attempt to determine which patients should be treated with reduction, some authors have investigated the relationship between sagittal spinal parameters and pelvic morphology and orientation. Patients with high-grade spondylolisthesis could be classified on the basis of the orientation of the pelvis as having a "balanced" or unbalanced" pelvis. The balanced pelvis type of spondylolisthesis includes patients with low pelvic tilt and high sacral slope, whereas the unbalanced type includes patients with a retroverted pelvis having a high pelvic tilt and low sacral slope. On the basis of this classification, some authors suggest reduction of the deformity, restoring the spinopelvic balance, only in patients with an unbalanced pelvis, whereas arthrodesis in situ without correction would be preferred in patients with a balanced pelvis. Although reduction can potentially result in complications, complication rates in the present analysis did not differ between the reduction and arthrodesis in situ groups. On the other hand, reduction of a high-grade spondylolisthesis would improve overall spine biomechanics by correcting the local kyphotic deformity and reducing the vertebral slippage. We manage patients with high-grade spondylolisthesis by performing reduction under intraoperative neurophysiologic monitoring such as SSEPs combined with spontaneous electromyography. We usually perform a posterolateral or circumferential instrumented arthrodesis. In conclusion, we found no definite benefit of reduction over arthrodesis in situ except for a significantly lower rate of pseudarthrosis. Further adequately powered randomized trials with appropriate subjective and objective outcome measures are required to establish evidence-based surgical management of high-grade spondylolisthesis."

The current surgical practice for low to medium grade spondylolisthesis reduction employs the use of pedicle screws with connective rods. Wherein the surgeon measures the amount of reduction required to realign the vertebrae and then uses the connecting rod to pull the upper vertebral body back causing a lever type action and placing the rod fastener into the tulip connection to fix the connections. As one can appreciate, this current best practice is at best an estimate of final reduction, due in part to a lack of control; the final results are typically a compromised approximation, but not a true alignment. Often this procedure of moving the adjacent vertebral bodies closer to alignment is a sufficient improvement to help the patient; however, this inability of the surgeon to precisely control the reduction is far from ideal. Furthermore, if the reduction achieved is less than satisfactory, the surgeon must start over loosening the rod and repositioning the pedicle screws, thus extending the surgical procedure.

The ideal reduction procedure would allow the surgeon to accomplish the reduction by controlling the movement in a consistent reliable and adjustable fashion so the exact optimal alignment is always achieved in the absence of predicting the preferred location, but rather controlling the movement to that exact location. Most importantly, this ability must occur in a timely fashion without unduly extending the surgical procedure.

The present invention as described herein accomplishes all these objectives and does so in typically less than 5 minutes added surgical time, most typically less than 4 minutes. Most advantageously, the system of the present invention is so accurate and reliable it virtually eliminates any need to redo the steps as there is no estimation made as to final placement, but rather a controlled movement to alignment which is fixed by the independent adjustment capability of the device in the hands of the surgeon aided by fluoroscopic vision.

These and other features of the system and its components afford new techniques in lumbar and thoracic spine surgery for use in a variety of indications as explained hereafter and shown in the attached drawings.

SUMMARY OF THE INVENTION

A method of treating and correcting a spinal misalignment is summarized in the steps: after exposing the spine and preparing it for instrumentation; Step 1—place MAC Pins bilaterally into the affected vertebral body, then one places standard top loading tulip pedicle screws into the vertebral body below. The listhesed segment such that two vertebral bodies are instrumented. Next a contoured rod is chosen based on the distance between the macpin and the pedicle screw discovered interoperatively. This rod is secured in an opening in the caudal edge of the coupler with a nut in the contoured position. The coupler is then slipped over the MAC Pin down into the surgical wound with the caudal edge of the rod falling into the top loading tulip of the pedicle screw below. At this point, the end cap is placed on the standard pedicle screw in the tulip and is tightened into position locking rods in the bilateral pedicle screws into a monoaxial and fixed relationship with regard to the instrumented vertebral bodies, the pedicle screws and the rods. The next step is to place the cannulated reduction tower over the macpin and through clockwise rotation of the reduction tower the listhesis is reduced in a slow, controlled and accurate method until the interoperative fluoroscope indicates a satisfactory reduction thus appropriate sagittal alignment. At this point, the second nut on the coupler is tightened with a wrench and this locks the entire construct into a rigid position therefore securing the spondylolisthesis reduction in place. The outer cannulated tower is then removed and the MAC Pins are sheared off flush with the coupler. It is at this point a laminectomy or decompression of the neural elements can be performed if so desired. Following the laminotomy, an interbody preparation fusion and graft placement can then take place. An alternative method would be to close the surgical wound and perform an anterior lumbar interbody fusion or a lateral transpsoas interbody fusion according to the pathology, indications and surgeon's surgical strategy.

A spinal alignment correction system has an elongated shaft and a rod coupler assembly. The elongated shaft has an inner pedicle screw portion with pedicle threads, an outer second thread portion with second threads and a transition or intermediate portion disposed between the pedicle screw portion and the second thread portion. The rod coupler has a pair of openings, a first opening for passing over the elongated shaft and being movable lengthwise within the transition or intermediate portion and a second opening for receiving a rod. The rod coupler is rotationally movable about said shaft. The spinal alignment correction system further has a cannulated tower. The cannulated tower has a longitudinally extending opening having internal threads complimentary to said second thread of said elongated shaft. The cannulated tower when mounted over said elongated shaft abuts said coupler along an outer cam surface and further tightening rotation of the cannulated tower causes outward movement of the elongated shaft. The spinal alignment correction system further has a handle removably attached to the cannulated tower to facilitate rotation of the cannulated tower. The spinal alignment correction system further has a rod fastener, said rod fastener when attached to said rod connector locks a rod securely fixed in the rod receiving opening. The spinal alignment correction system further has a washer and a locking nut for attachment onto the coupler and abuttingly locking said washer against said coupler.

The spinal alignment correction system further has a rod, a rod fastener and a pedicle screw with rod receiving connection. The pedicle screw when affixed to a lower vertebral body has the rod extend to the second rod receiving opening of the rod coupler positioned over the elongated shaft affixed to an upper vertebral body, when the rod is at one end is placed in said rod receiving connection of the pedicle screw and fixed by said fastener, the opposite rod is placed in the second rod opening of said coupler and fixed to said coupler after a desired vertebral alignment is achieved. The elongated shaft preferably is made of titanium.

BRIEF DESCRIPTION OF THE DRAWINGS

The invention will be described by way of example and with reference to the accompanying drawings in which.

DETAILED DESCRIPTION OF THE INVENTION

Figure 1:
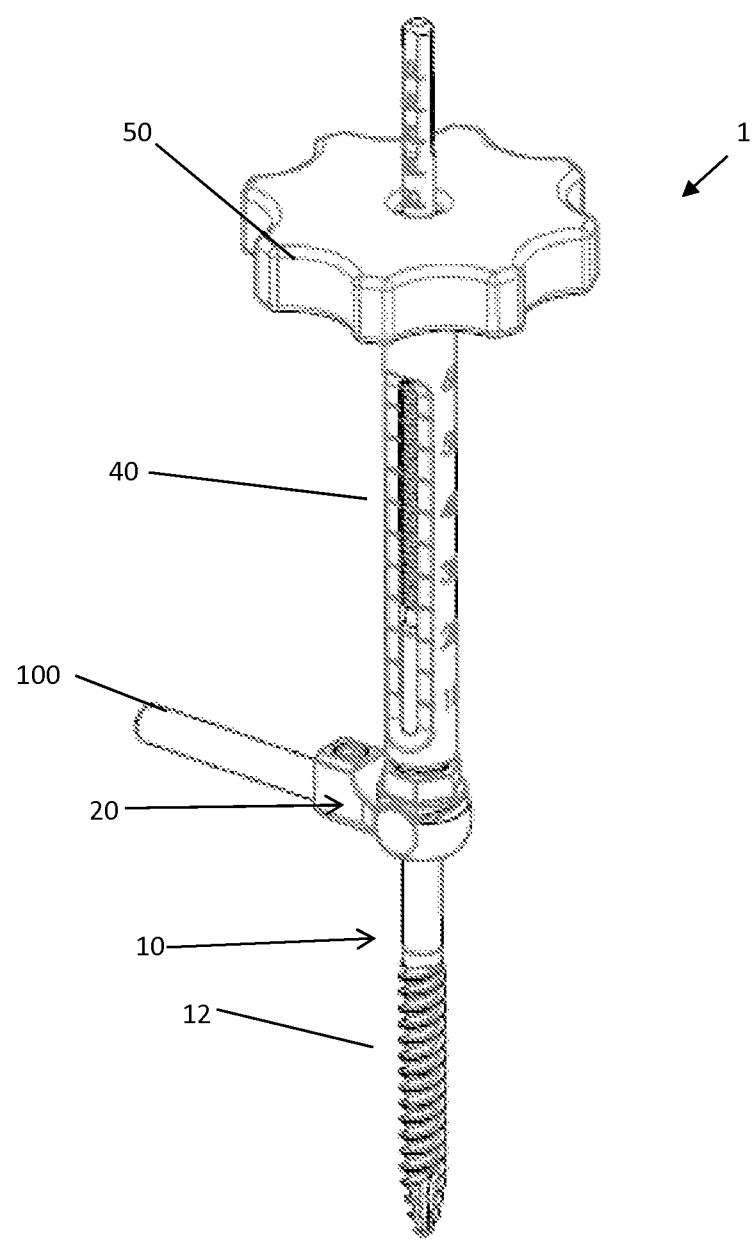
FIG. 1 is a perspective view of the system or device of the present invention.
Figure 1A:
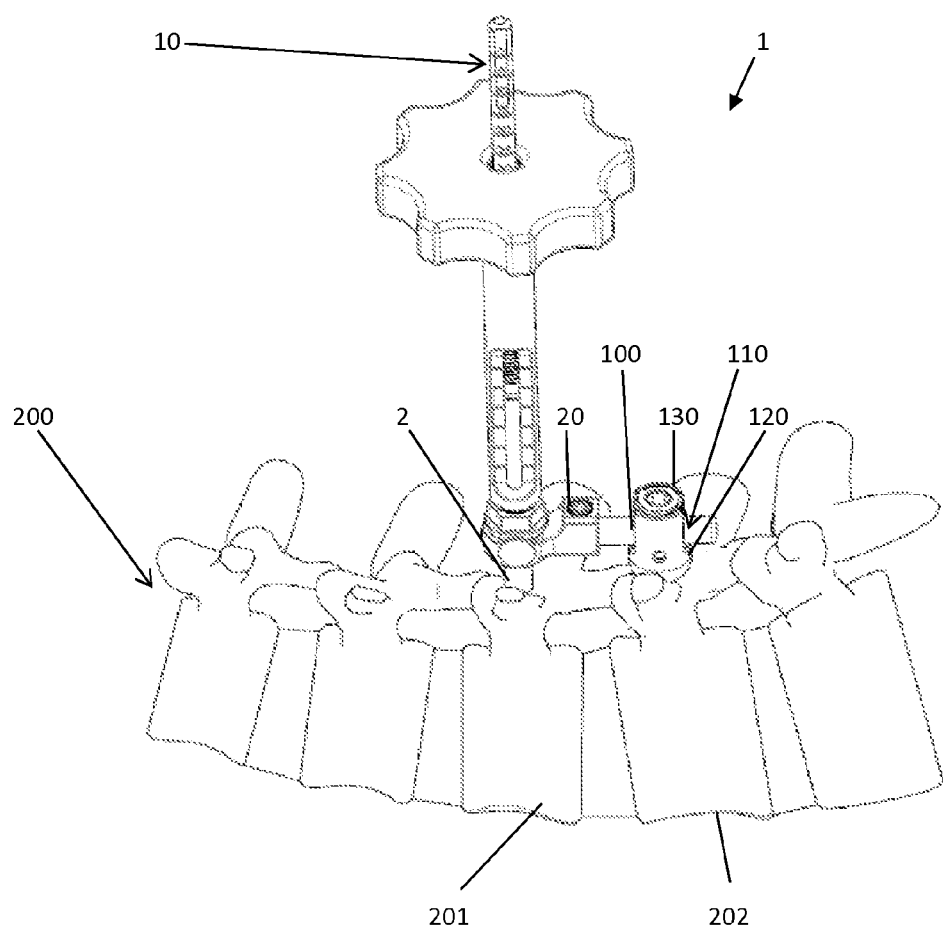
FIG. 1A is a view of the system of FIG. 1 installed in a spine segment.
Figure 2:
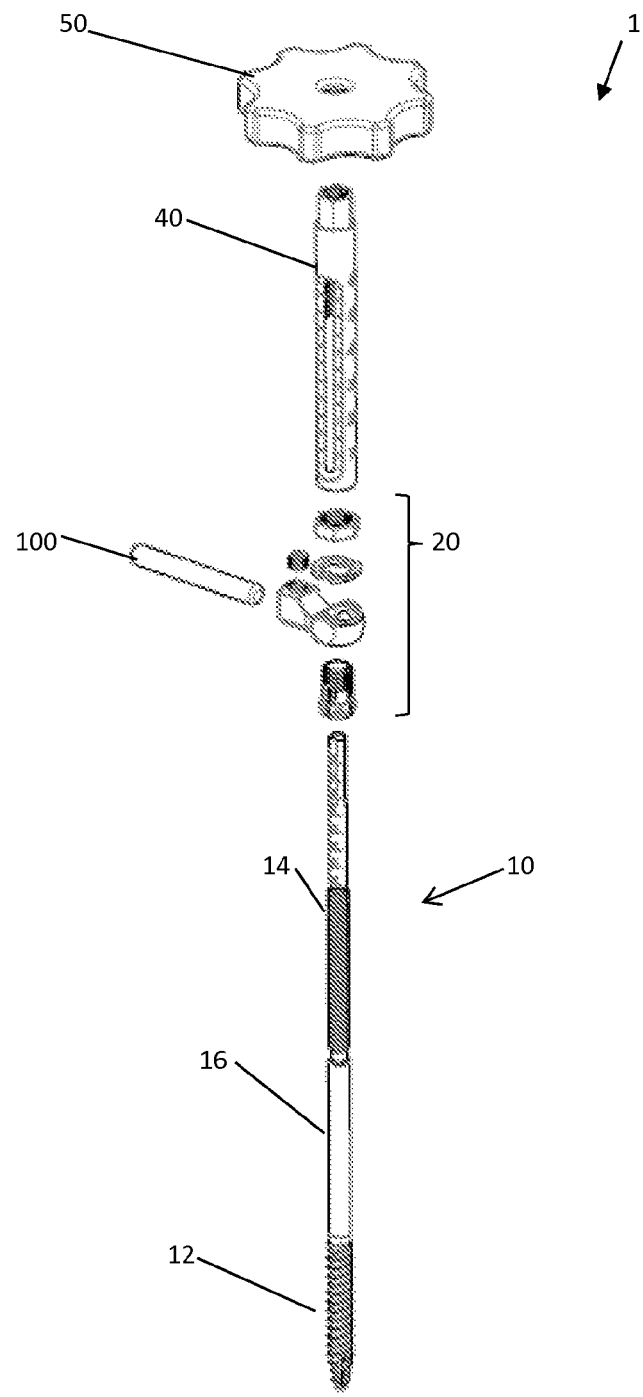
FIG. 2 is an exploded view of the present invention of the system shown in FIG. 1.

The following description is best understood by reference to the attached drawings depicting one embodiment of the present invention. With reference to FIGS. 1, 1A and 2.

The device or spinal alignment system 1 is shown as described has a double threaded post lumbar pedicle screw 10 hereinafter also referred to as a Maximum Alignment Correction Pin (MAC Pin) that is placed in the vertebral body 201 and coupled with a special screw rod coupler or coupler assemblies 20 and that adjoins the posted screw 10 to a rod 100 connected into a lower vertebral body 202 of a particular segment of the spine 200. The posted screw 10 is attached to the rod 100 and the other end of the rod 100 attached to a typical pedicle screw 110 placed in the vertebral body 202 below. The device or system 1 will include a double threaded post lumbar/thoracic pedicle screw thread end portion 12 on the screw 10 as well as a coupler 20 and there is also a technique for using this implanted device or system 1.

Figure 3:
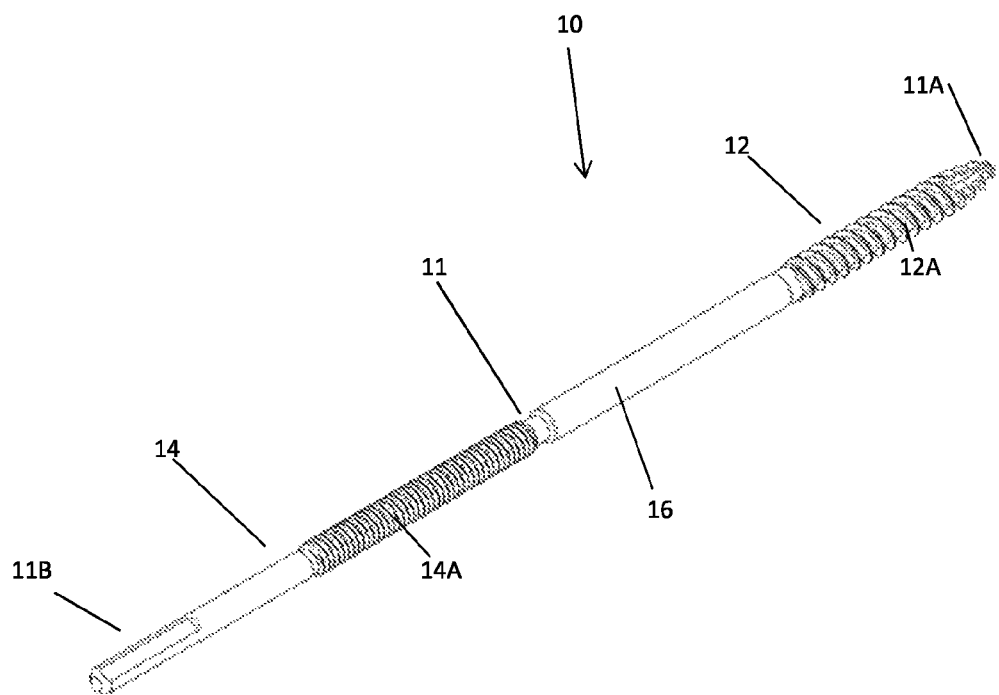
FIG. 3 is a perspective view of the posted pedicle screw or MAC Pin.
Figure 3A:
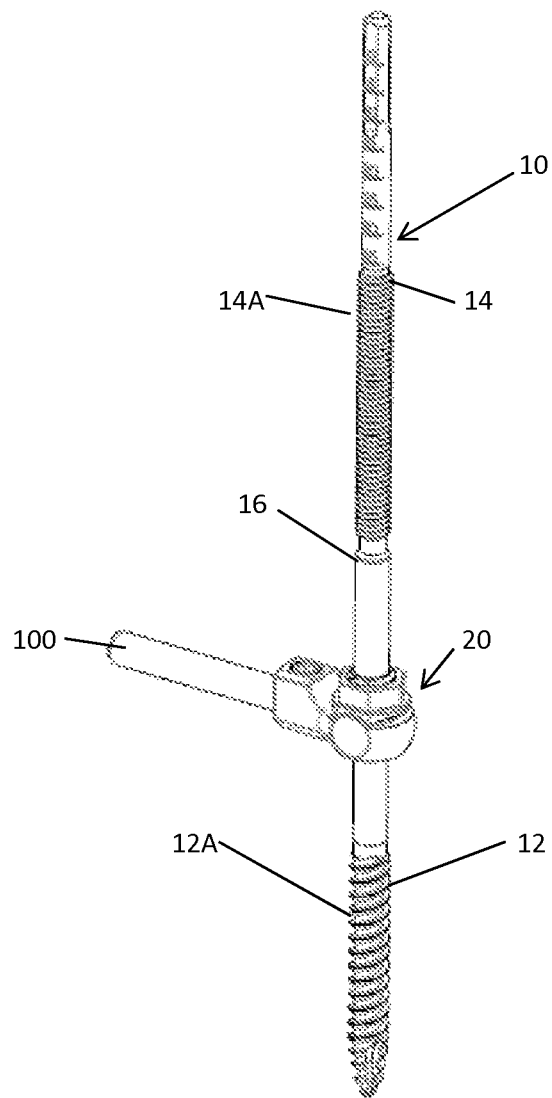
FIG. 3A a view of the MAC Pin with rod coupler assembly.

As shown in FIGS. 3 and 3a, this posted pedicle screw 10 has a one piece shaft 11 with a double threaded pedicle screw thread 12 of a typical pedicle screw. The elongated shaft having an overall length of at least 100 mm. The thread 12 extends from a leading tip 11A to a length at least 40 mm, preferably of about 50-55 mm in length up the shaft 11, thereafter the posted screw 10 has a transition portion 16 which can be a smooth shaft portion between two threaded portions. The pedicle threads of the screw 10 are in the range of 5.0 to 8.0 mm in size, more typically between 5.5 and 7.5 mm and have a self-tapping feature as shown at end 11A. A second thread 14 at the other end of the shaft 11 of the screw 10 of the screw is used for the actual reduction or translation technique. The outer end 11B of the second screw portion 14 that will be sticking out of the spine 200 may have a squared off or flat feature that will be able to connect to a handle or wrench that will allow the posted pedicle screw 10 to be installed into the vertebral bone 202, independent of the the rod coupler 20. This shafted post pedicle screw 10 is called the MAC Pin (Maximum Alignment Correction Pin). For the first time this pedicle screw 10 and coupler 20 enables the vertebral body 201 to be pulled back in the sagittal plane to be realigned with the other vertebral bodies 202 to establish perfect mechanical alignment, restore the mechanical alignment of the spine 200, believed to be the best outcome for the patient. The coupler 20 enables the tip 11B of the posted pedicle screw or the MAC Pin 10, once the pedicle portion 12 of the MAC Pin 10 has been placed within the vertebral body 201 of the lumbar spine 200, to be pulled back. That threaded portion 14 will be used to pull the vertebrae 201 back 35-50 or 65 mm. The coupler 20 is slipped over outer the tip 11B of the MAC Pin 10, the coupler 20 as an assembly, but untightened, falls into the spine interoperatively into the smooth shaft transition portion 16 of the MAC Pin 10 between the two threaded 12 and 14 areas of the MAC Pin 10. The coupler 20 is attached to an end of a contoured rod 100 which when placed down over the MAC Pin 10, the opposite end of that rod falls into the top of aa top loading tulip 120 of the tulip headed pedicle screw 110 in the vertebral body 202 below, see FIG. 1A. When the coupler 20 fixed to the rod 100 is placed within the pedicle screw 110 this enables not only translation again also distraction or compression of the motion segment 202 between the two vertebral bodies 201, 202. Once this assembly is accomplished, the technique can begin.

With referenced to FIGS. 3A, 4, 4A and 4B the rod coupler assembly 20 is shown, the coupler 20 has two holes 21, 22, one hole 21 is able to slip over the posted pedicle screw or MAC Pin 10 and then the other hole 22 will allow the contoured rod 100 to fit within it and then prior to placing the coupler 20 and rod 100 over the posted pedicle screw or MAC Pin 10 the surgeon will lock the rod 100 by choosing various lengths of rods according to what is discovered as needed interoperatively with the 5.5 diameter rod 100, the rod 100 will slip into the caudal edge of the coupler 20. Once the rod 100 is slipped into the caudal edge, there is a separate nut or set screw 102 and tightener that tightens this rod 100 in place into the threaded opening 103 of the coupler 20.

Figure 4:
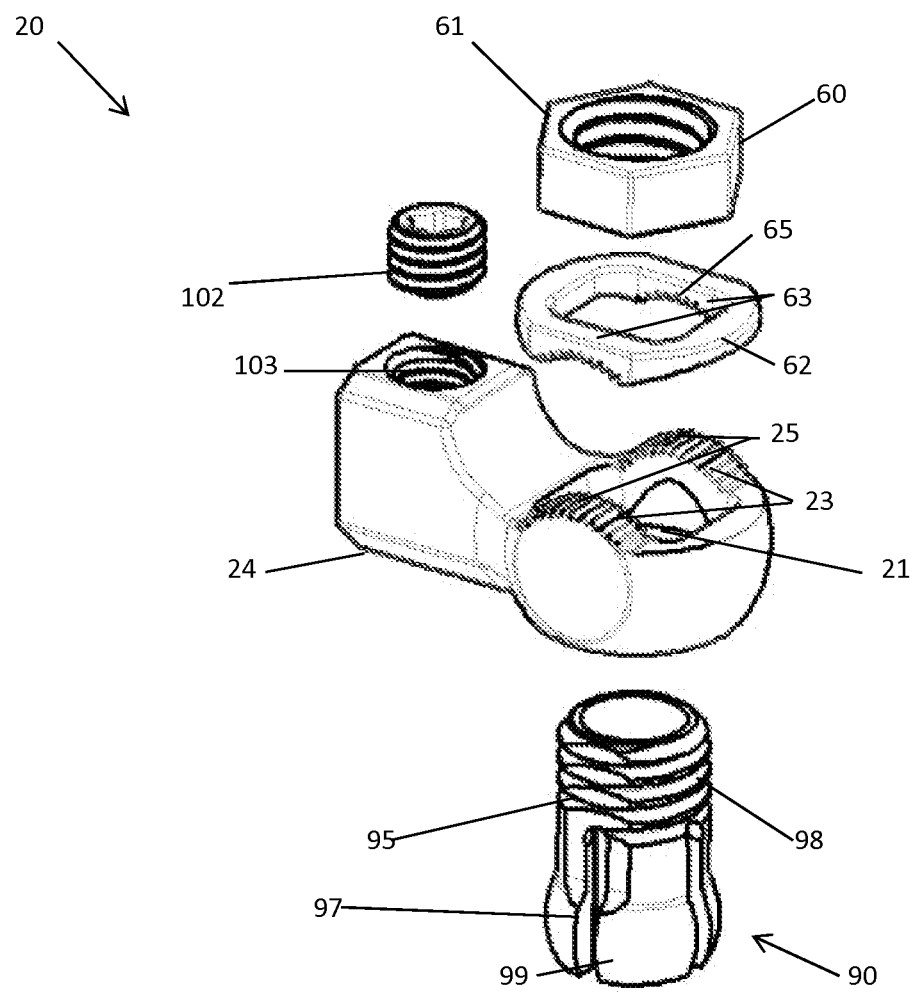
FIG. 4 is an exploded view of the rod coupler.
Figure 4A:
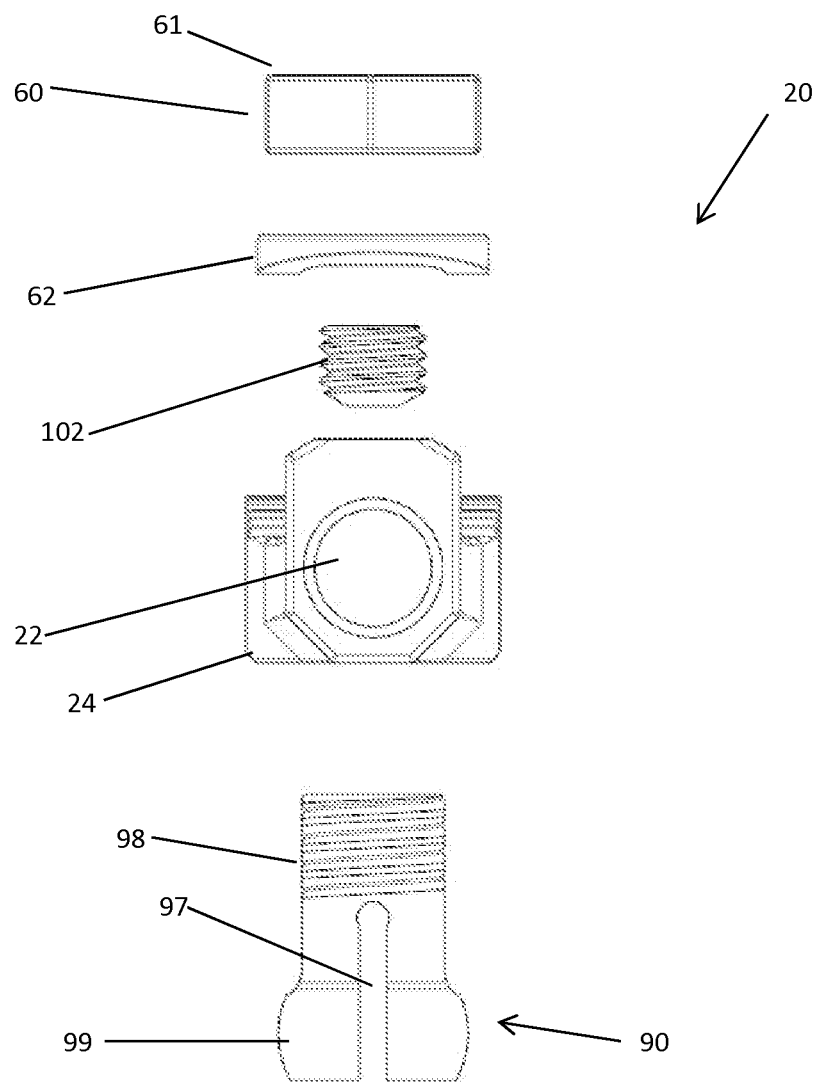
FIG. 4A is an exploded side view of the rod coupler.
Figure 4B:
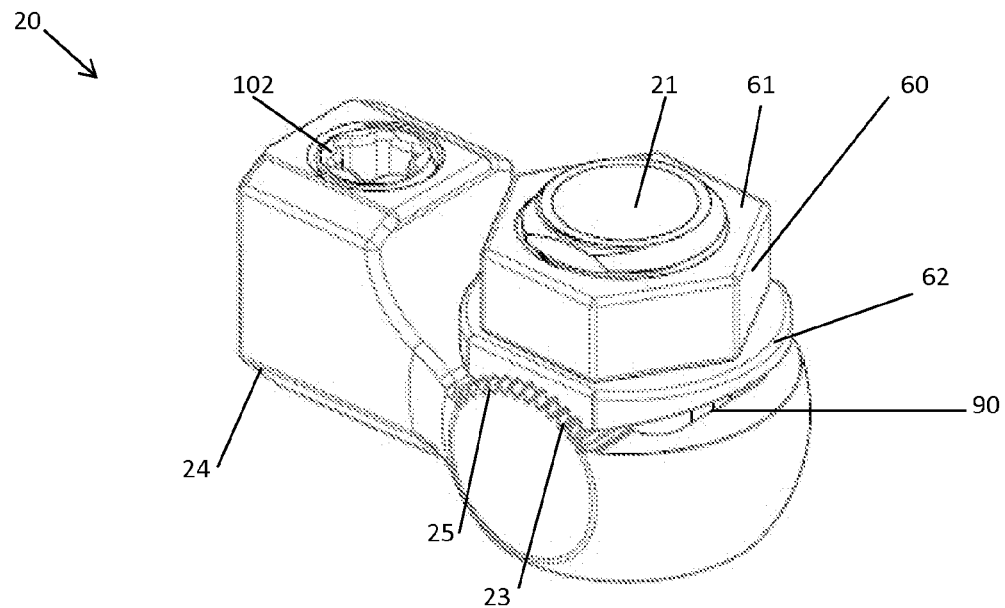
FIG. 4B is an as assembled view of the coupler.

As shown in FIGS. 4, 4A and 4B, the rod coupler assembly 20 has a coupler body 24 which has the openings 21 and 22 for receiving and holding the MAC Pin 10 and rod 100 respectively. At the bottom of FIG. 4 is a hollow shaft holding coupling 26 with a threaded end 98 and an opposite rounded or spherical end 99 with a plurality of slots 97 to allow the end 27 to grip the MAC Pin 10 when the coupler assembly nut 60 is tightened against the washer 62 and the teeth 25 serrated sidewalls 23. The washer 62 having complimentary serrated teeth 65 that interlock as the nut 60 threads onto the threads 98 of the shaft holding coupling 90. Initially, the entire coupling assembly 20 is connected, but loosely so the coupling can slide freely over the MAC Pin 10 and move angularly about the smooth shaft portion 16. Only when the proper vertebral body alignment is achieved by the use of the cannulated tower 40 and the handle 50 is the nut 60 tightened locking the coupler 20 onto the MAC Pin 10 fixing its position. As noted, all the parts aligned with opening 21 have openings allowing the MAC Pin 10 to pass as shown. The shaft holding coupling mechanism 90 provides for limited angular motion of the MAC Pin 10. Nevertheless, this ability to tilt the assembly is beneficial to the installation of the instrumentation. As further illustrated, the system 1 further has a cannulated reduction tower or shaft 40 mounted over the MAC Pin 10 and resting on a nut 60 of the coupler assembly 20. Above and removably affixed to the tower 40 is a handle 50 which is used to rotate the cannulated reduction tower 40 as the system 1 is employed to align the vertebral body 202 in the spine 200.

Once the rod 100 and coupler 20 are joined through this nut 102, a fixed relationship is established between the rod 100 and coupler 20. At that point, the other end, the cranial end, of the coupler 20 would then slip over the MAC Pin 10 until the coupler falls into the dorsal aspect of the bone of the vertebral body 201 which is the base of the lumbar pedicle and also at that point it will be positioned within the smooth shaft portion 16 of the MAC Pin 10, the threaded pedicle portion 12 of the MAC Pin 10 would have been driven transpedicularly into the vertebral body 201 where whatever length has been chosen of the threaded pedicle portion 12 of the threads 12A will be countersunk into the vertebral body and pedicle shaft. This can be anywhere from 35 mm up to 50-65 mm within the vertebral body 201. At this point, sticking out of the posterior aspect of the pedicle and vertebral body 201 would be the MAC Pin 10, the smooth shaft portion 16 and also the second thread portion 14 as well as the squared off tip 11B. So when the coupler 20 slips over the post MAC Pin 10, the coupler 20 is positioned within the smooth shaft portion 16 enabling it to more or less cam back and forth on the MAC Pin 10 so that a smooth frictionless relationship exists with the MAC Pin 10 and the rod. At this point again, simultaneously when the coupler 20 and the rod 100 are slipped over the MAC Pin 10, the caudal of the 5.5 rod 100 would fall down into the opening of the tulip 120 the top loading tulip pedicle screw 110 and the vertebral body 201. At that point, the end fastener cap 130 on the tulip 120 of the top loading pedicle screw 110 would be placed and the end cap 130 would be tightened after whatever distraction or compression is desired. Once the coupler 20 and the rod 100 slide down over the MAC Pin 10 and fall within the tulip 120, the end cap 130 of the tulip 120 would then be placed. At this point, a distractor or a compressor can be utilized to distract between the MAC Pin 10 from the pedicle screw 110 once it achieves distraction of the this or the posterior neuroforamen, independently of the translation of the vertebral body 201 that follows this distraction. Once distraction or compression is accomplished, the end cap 130 and the posted pedicle screw 10 below would be tightened and then the rod 100 and the posted pedicle screw 10 relationship would become fixed. At that point the only motion that is still available between the MAC Pin 10 and the pedicle screw 110 below or at the rod 100 is the translation or the reduction of the spondylolisthesis.

Figure 7:
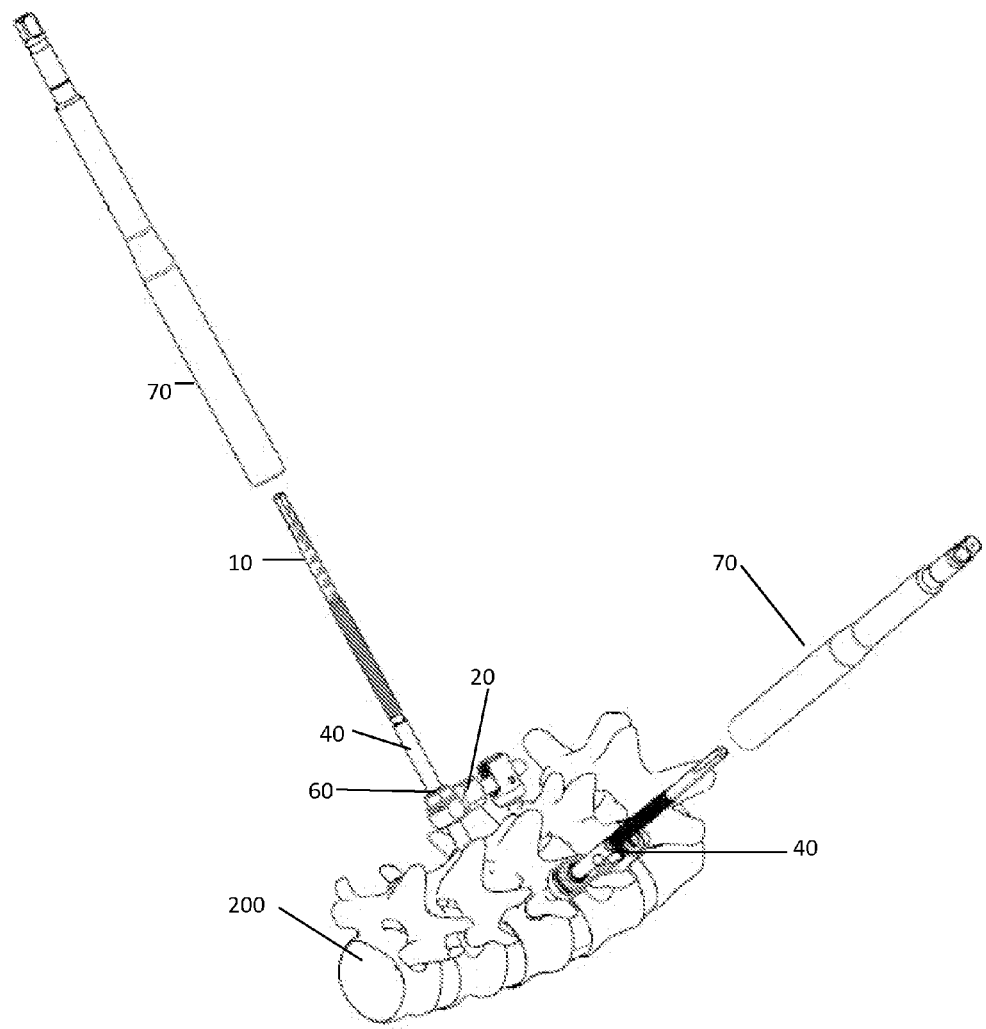
FIG. 7 is a view of the wrenches shown above MAC Pins and cannulated towers of the system for final nut tightening.
Figure 7A:
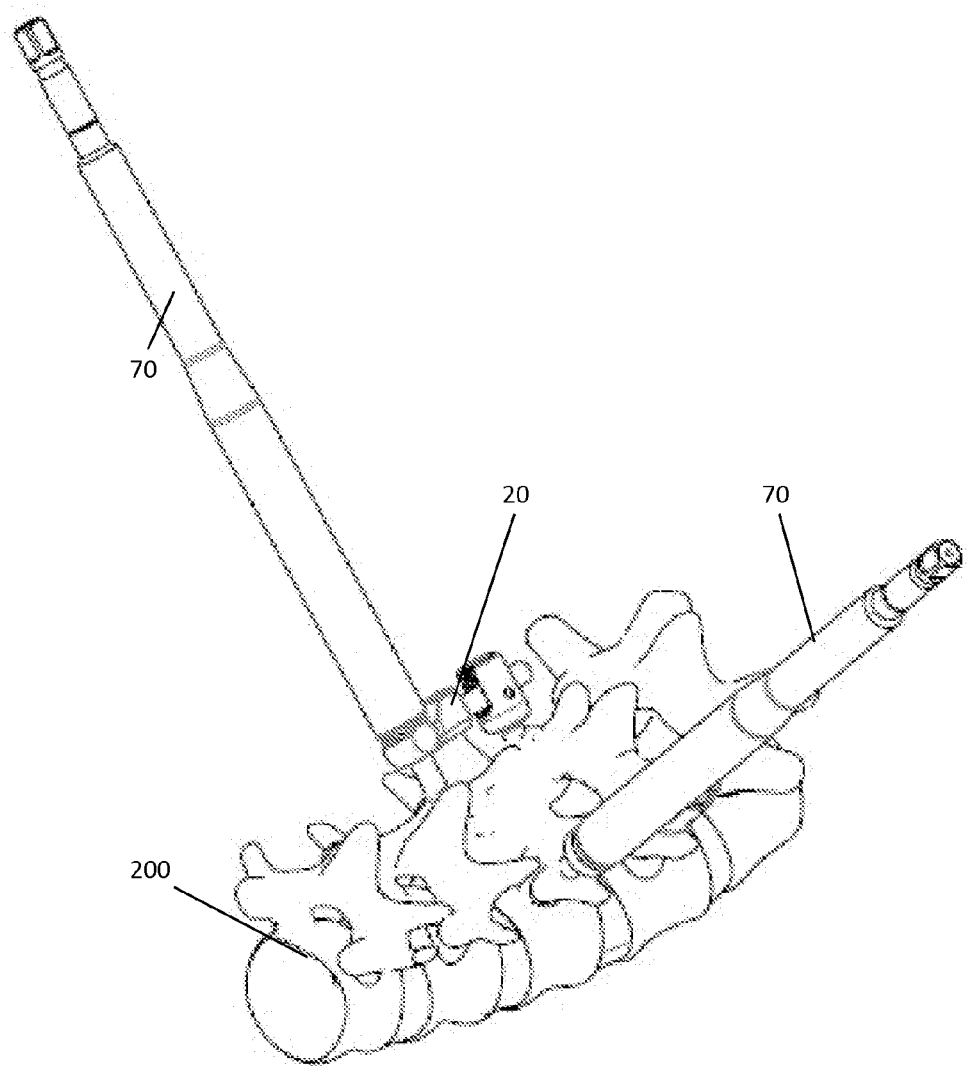
FIG. 7A shows the wrenches in place over the system to provide final nut tightening to fix the MAC Pin to the coupler.
Figure 8A:
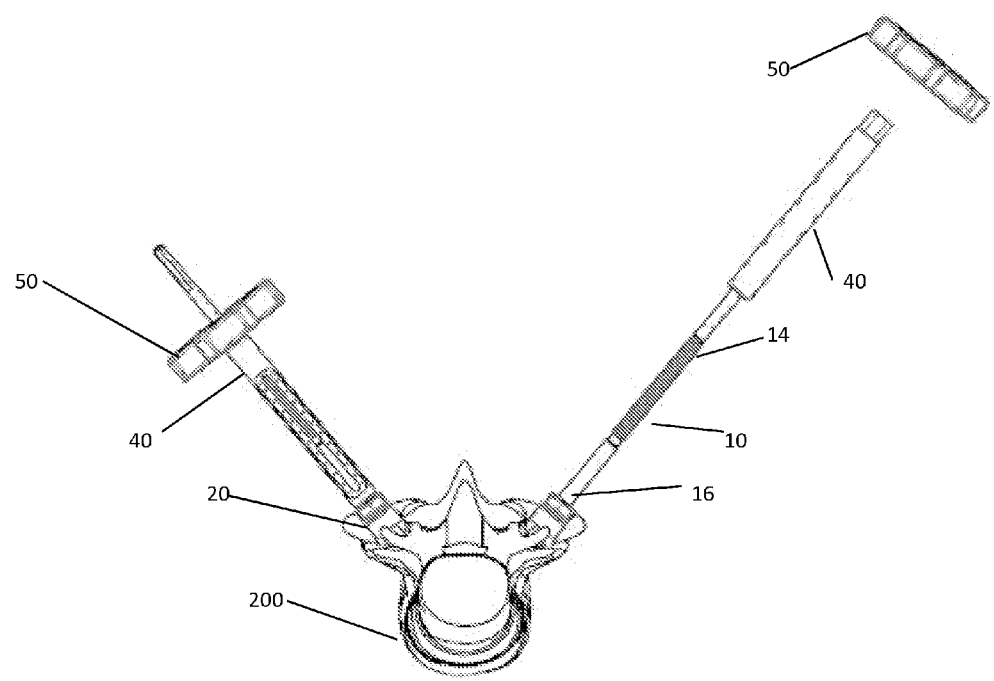
FIGS. 8A-8J are various views of spines having the system of the present invention used showing the various steps employed.
Figure 8B:
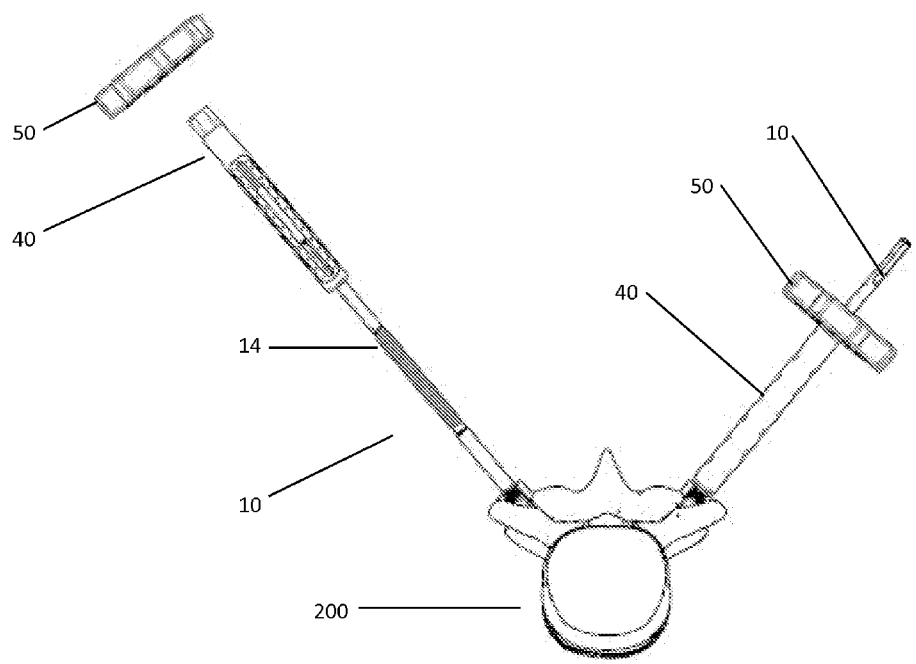
Figure 8C:
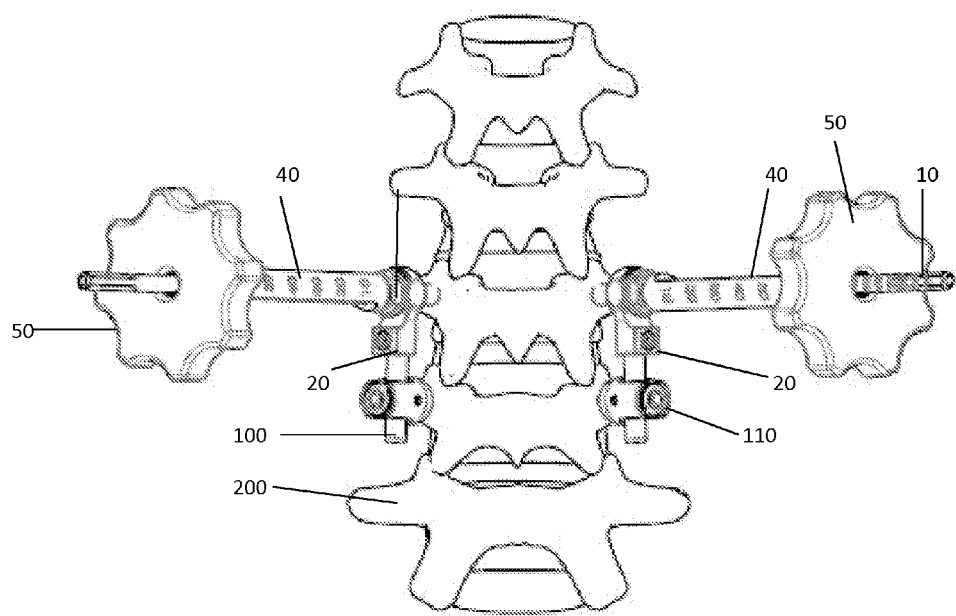
Figure 8D:
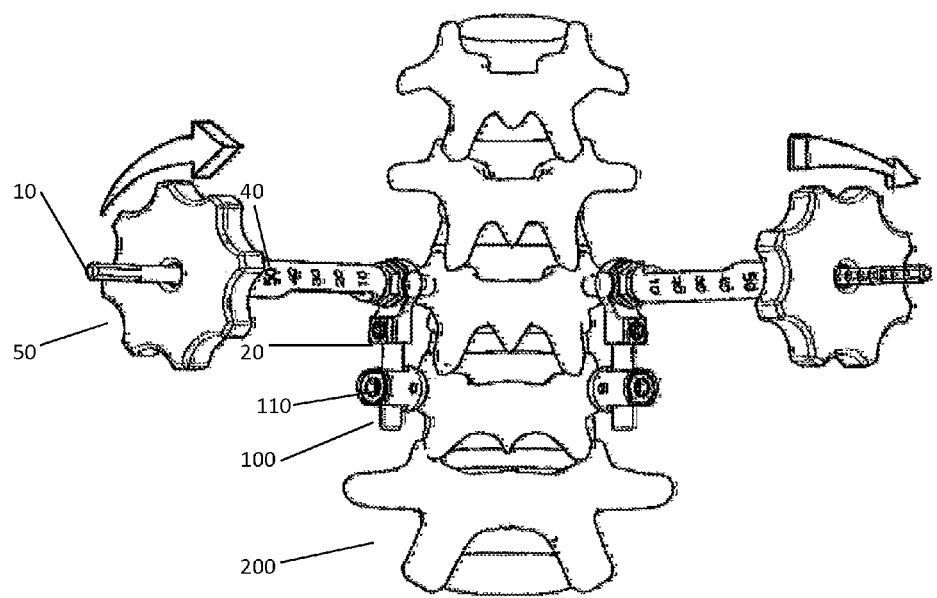
Figure 8E:
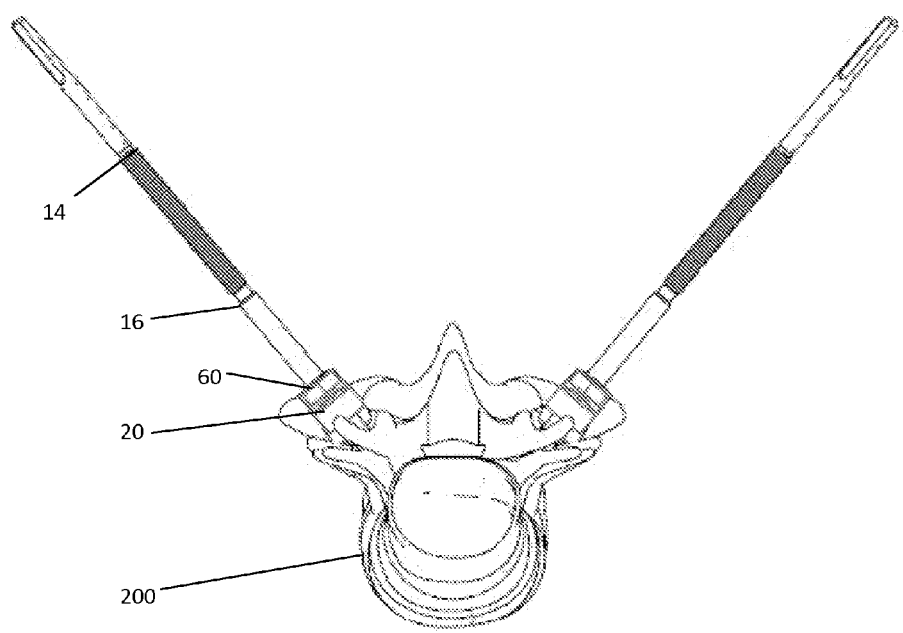
Figure 8F:
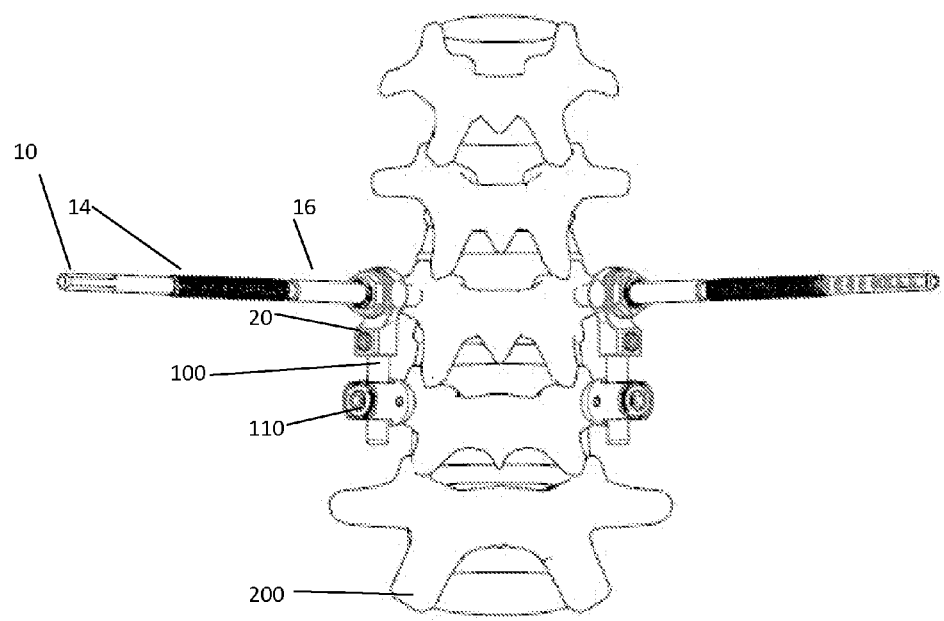
Figure 8G:
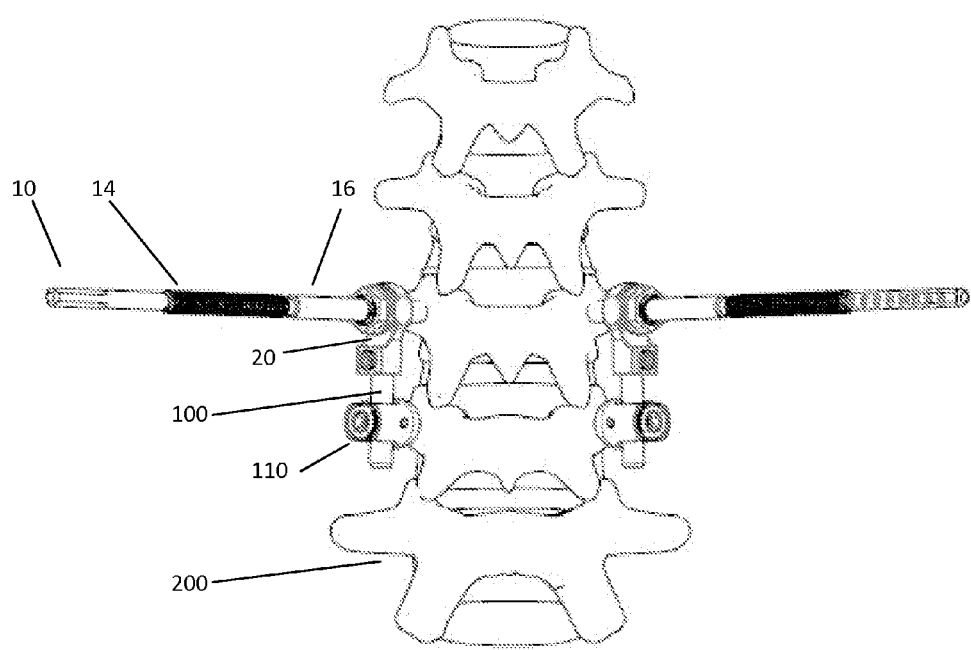
Figure 8H:
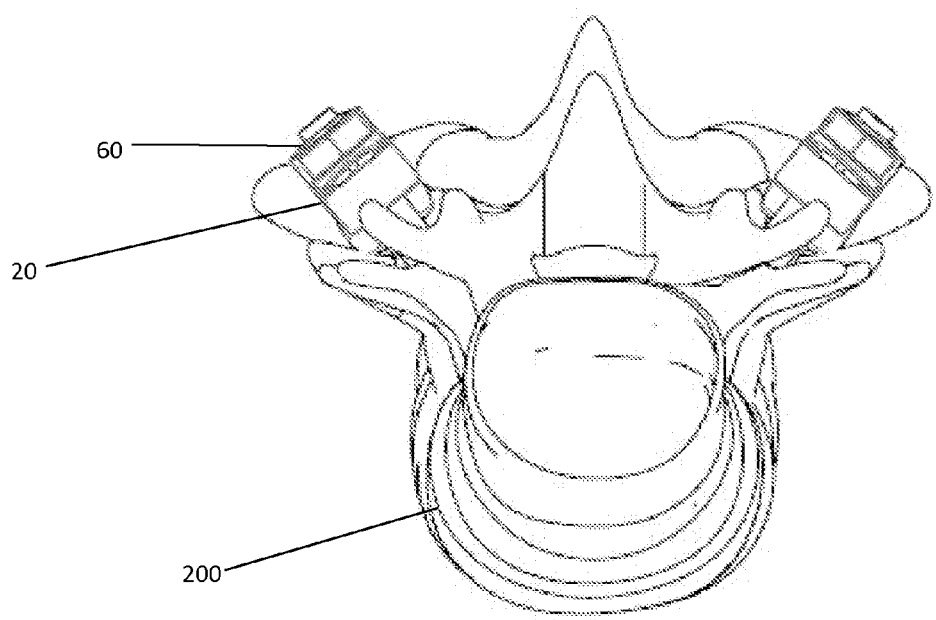
Figure 8I:
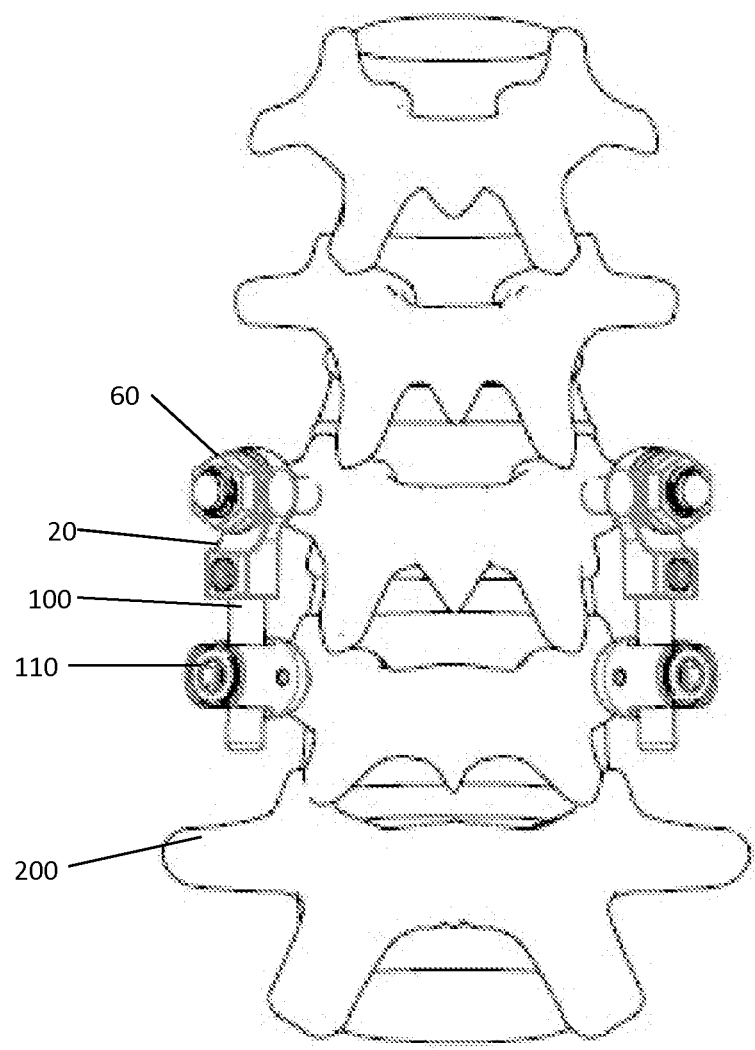
Figure 8J:
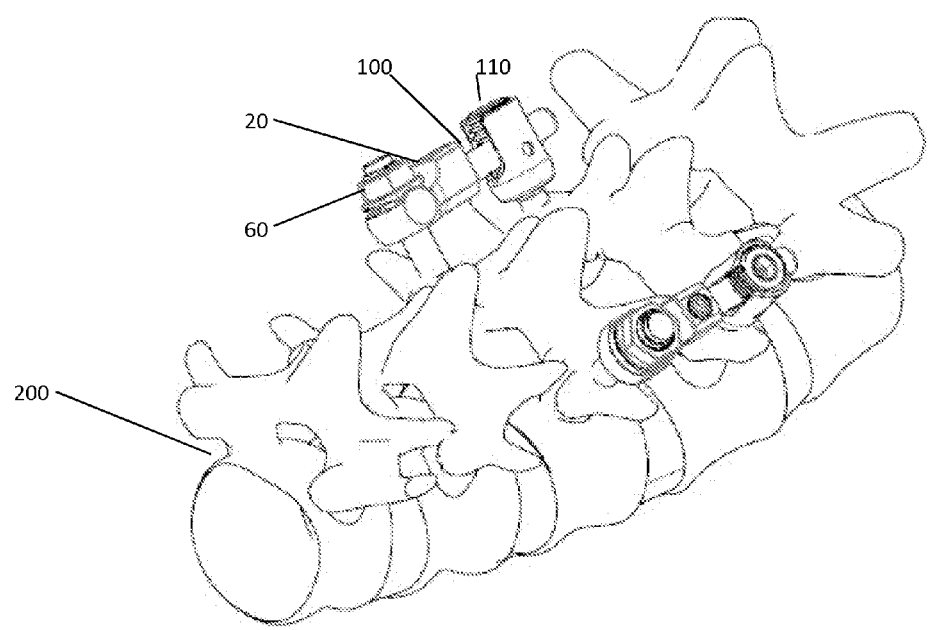

To visually appreciate the procedure, after the MAC Pins 10 have been inserted bilaterally, the surgeon would place the coupling assembly 20 over the MAC Pin 10 as shown in FIGS. 8E-8G and lock the connector rod 100 to the pedicle screw as discussed. Thereafter, the cannulated towers 40 and handles 50 would be placed over the MAC Pins 10 as shown in FIGS. 8A-8D. At this point, the rod coupler assembly is assembled, but is loose sitting over the smooth shaft portion 16 free to allow the MAC Pin 10 to be retracted. As shown in FIG. 8D, once the towers engage the second threads 14A by rotation of the handle 50, the MAC Pins 10 are refracted. The tower 40 abuts on the top or outer cam surface 61 of the nut 60 which acts as a cam. Importantly, as the tower 40 rotates, the MAC Pin 10 does not rotate, but rather moves longitudinally in the direction of the handle rotation. In this way, the pedicle portion 12 does not change neither tightening nor loosening. This allows the vertebral body 202 to retract toward alignment. Once the desired alignment is achieved, the handle 50 can be removed and a wrench 70, shown in FIGS. 7 and 7A, can pass over the tower 40 to securely tighten the nut 60 fixing and locking the rod coupler 20 to the MAC Pin 10. This occurs as the slots 97 at the end of the coupling mechanism 90 close about the shaft 11 at the smooth portion 16 of the MAC Pin 10. Once locked in position, the wrench 70 is removed and the cannulated tower 40 is removed from its attachment to the exposed second threaded portion 14 of the MAC Pin 10. Once removed, the surgeon cuts the MAC Pin 10 flush to the nut 60 of the rod coupler assembly 20 as shown in views 8H-8J.

Figure 9A:
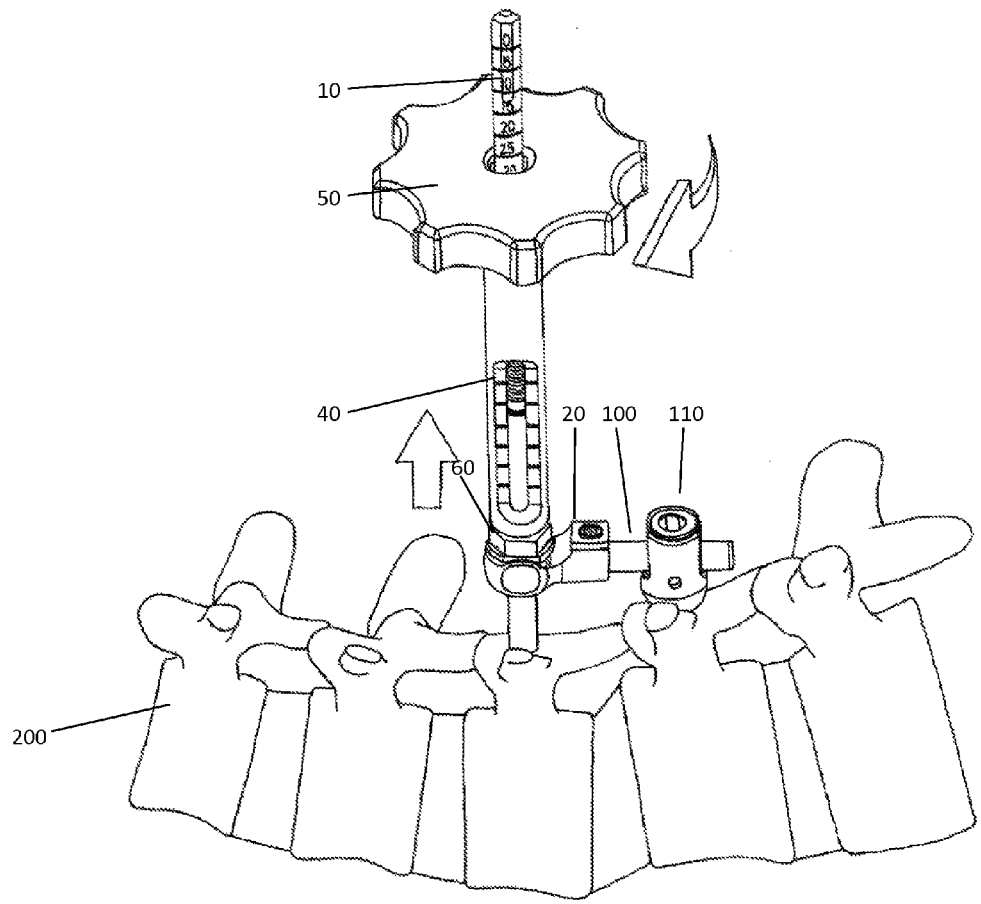
FIG. 9A is a side view illustrating a malaligned spine and a use of the system showing the reduction direction as the handle is rotated.
Figure 9B:
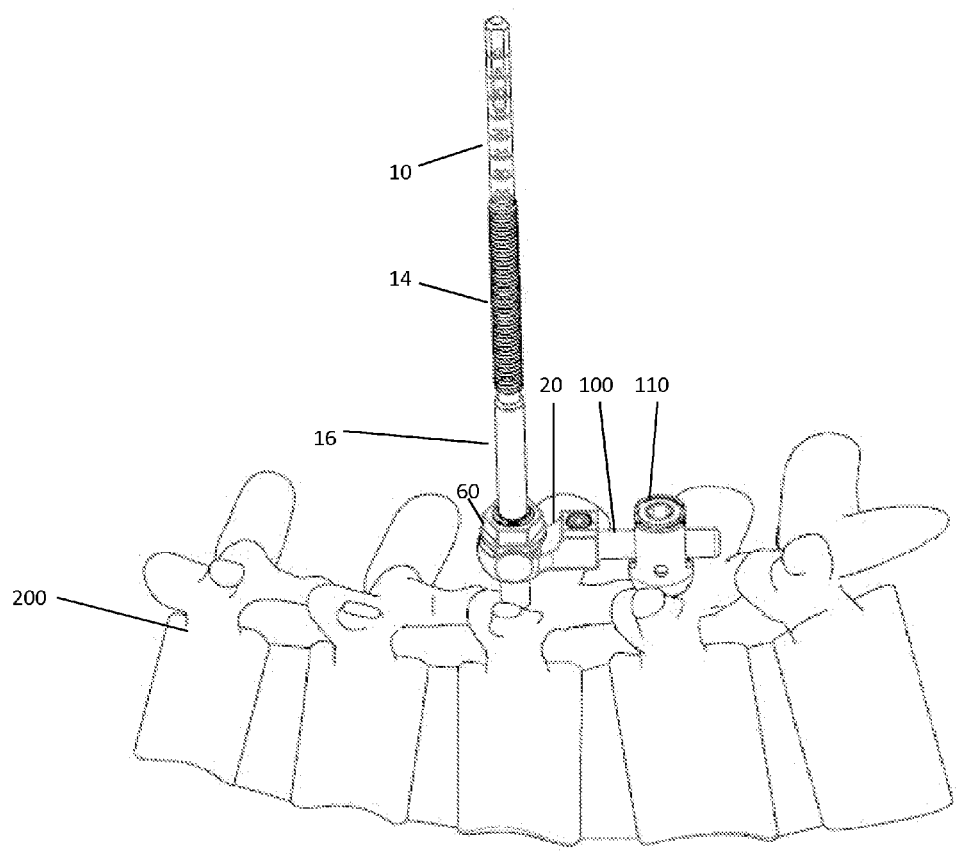
FIG. 9B shows the corrected spine segment of FIG. 9A.

In FIGS. 9A and 9B an exemplary procedure of a spinal segment 200 is shown with the system 1 installed and being turned to retract the spondylolisthesis of vertebral body 202 as the rod 100 is fixed to the lower vertebral body 201 at the pedicle screw 111. Once alignment is achieved, the tower 40 is removed after the nut 60 is tightened, see FIG. 9B. This is accomplished preferably using two MAC Pins 10 bilaterally as previously discussed in reference to FIGS. 8A-8J.

Figures 5, 5A:
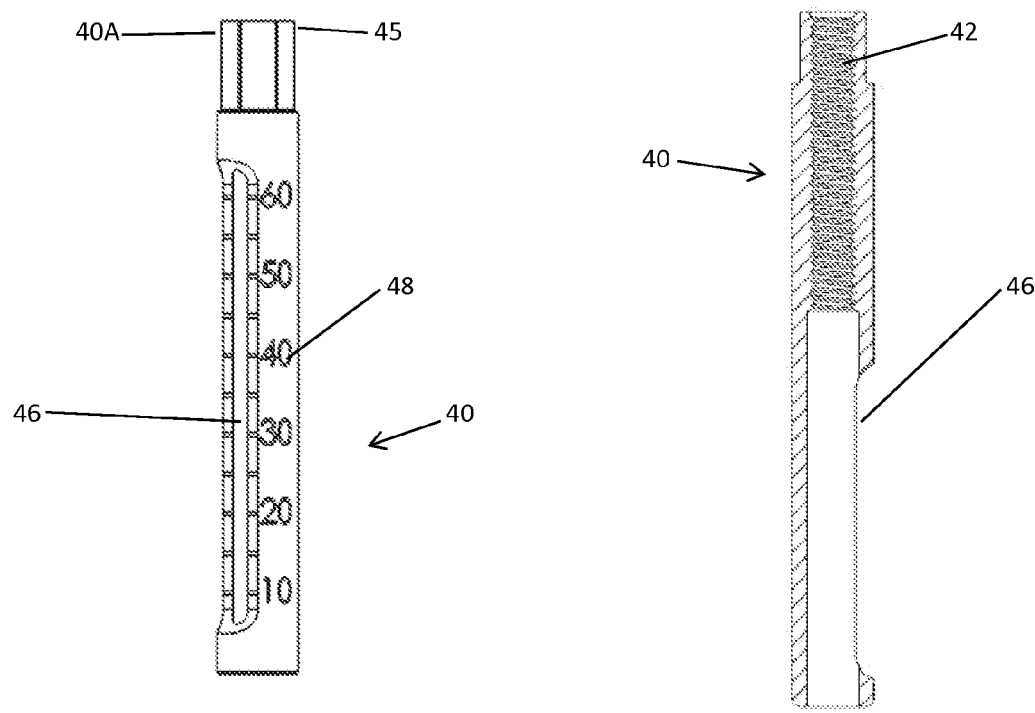
FIG. 5 is a side view of the cannulated tower.
FIG. 5A is a cross sectional view of the cannulated tower.

The next step would be slipping a cannulated tower 40, shown in FIG. 5 and cross section in FIG. 5A, over the exposed outer tip 11B of the MAC Pin 10 with a handle 50 on that cannulated tower 40. The cannulated tower 40 has an inner threaded portion 42 that threads onto the second set of threads 14A on the exposed MAC Pin 10. At this point, the handle 50 on the cannulated tower 40 is rotated moving the tower 40 over that threaded portion 14 of the MAC Pin 10 and as you move the handle 50, the cannulated tower 40 moves down the threads 14 until it abuts against the nut 2 of the coupler; the pedicle screw portion and rod relationship and begins to pull that vertebral body into a more aligned position such that the surgeon would be able to translate or reduce the spondylolisthesis anywhere between 1 mm up to 2-3 cm and this is a unique property of the system 10 in that no other system allows an independent translation and independent distraction and compression of the motion segment that is so accurate. Once you begin to translate the MAC Pin 10 on the coupler 20, it allows complete independent and accuracy whether or not you need 1 mm of reduction or 3 cm of reduction. The surgeon is able to dial that in interoperatively and stop at whatever point he wants between that 0 to 3 cm. There is no guesswork, no estimation, the surgeon simply begins to dial in the amount of reduction he wants and by checking interoperative fluoroscope he can judge when the reduction is complete and therefore stop the process at that point.

Figure 6:
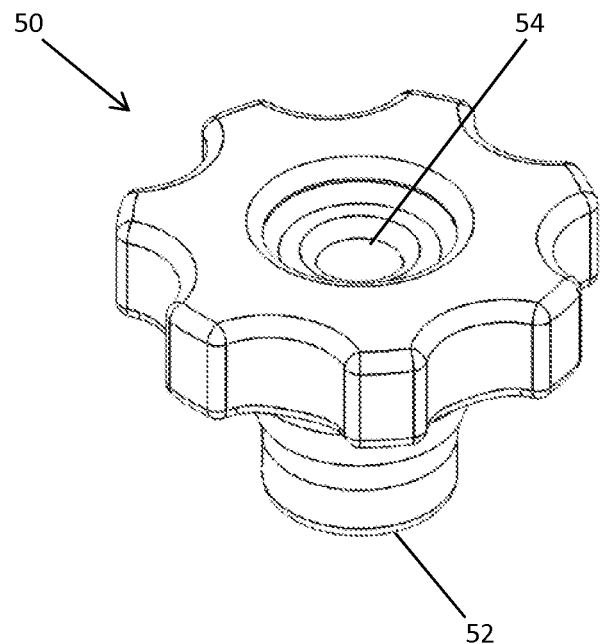
FIG. 6 is a view of an exemplary handle for use with the cannulated tower.
Figure 6A:
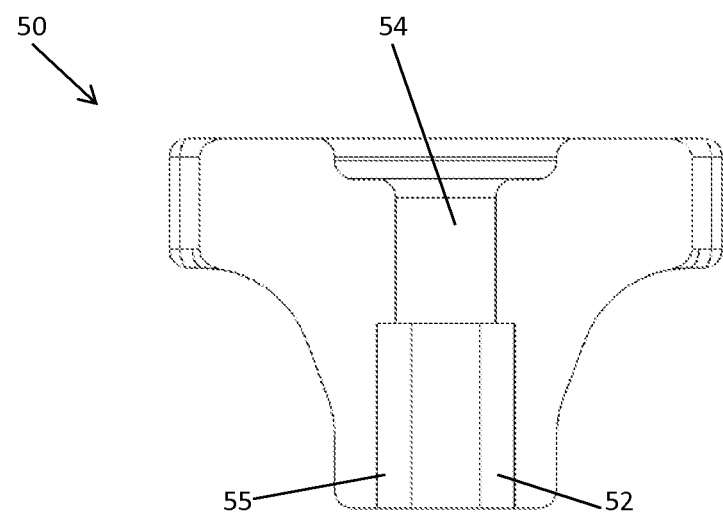
FIG. 6A is a cross section of the exemplary handle.

As shown in FIG. 5, the cannulated tower 40 has an end 40A with flats 45 to receive the handle 50. The tower 40, as shown, further has a window opening 46 which allows the surgeon to see the MAC Pin 10 movement. A graduated scale 48 marked 10-60 increments of 10 mm is provided adjacent the window opening 46. The handle 50, shown in FIGS. 6 and 6A, when placed onto the tower 40 has an opening 54 that allows the MAC Pin 10 to pass. The opening 52 receives the end 40A and has flats 55 to compliment the flats 45 to rotationally fix the tower to the removable handle 50.

Another unique feature of this system is the fact that as the surgeon reduces the spondylolisthesis, let's say for example 2 cm, and for whatever reason perhaps the nerve begins to show signal of being pinched, he can then go back and translate the vertebral body 201 forward again back to say 1 or 1.5 cm. Essentially, this device 10 gives the surgeon complete control of an accurate reduction, distraction and rotation of the vertebral body 202 like no other product does. Once the translation or rotation has been performed through the MAC Pin 10 and the cannulated tower 40 and handle 50, at that point a separate wrench 70 and nut 60 are placed over the cannulated tower 40 and the MAC Pin 10 being held in place. The surgeon, using the separate wrench 70, tightens a nut 60 on the coupler 20, this locks the relationship between the coupler 20 and MAC Pin 10 so that is now a fixed relationship and once that fixed relationship is achieved, then the reduction is complete and locked in. At that point, the wrench 70 comes off the cannulated tower 40 and then the cannulated tower 40 is removed from the MAC Pin 10 and then a MAC Pin cutter 80 fits over the exposed tip of the MAC Pin 10 and cuts the MAC Pin 10 flush with the coupler 20. Now the procedure is completed with a fully distracted or compressed and reduced vertebral body 202 in the spondylolisthesis. At this point, every relationship between the MAC Pin 10, the pedicle screw 110 and the rod 100 are locked down and fixed ensuring the spondylolisthesis has been exactly reduced. At this point, that would be the completion of the procedure.

Now the technique described above typically would be performed open, in an open procedure and also bilaterally with both pedicles and the right and the left side of the vertebral body that is in listhesis would be addressed. And then the procedure would alternate right versus left a little bit of reduction the right and then a little bit of reduction left, and then alternate the right to left so that the vertebral body is translated or reduced in a symmetrical fashion so that no undue rotation is performed during the reduction technique. And then after the reduction is complete, then again the MAC Pin 10 cut off flush to the coupler 20. This procedure can be performed on a one level spondylolisthesis, a two level spondylolisthesis or in a situation where a spondylolisthesis is a top 1-2 or 3 segments that need to be instrumented according to the indications of the particular surgeon.

This procedure can also be done percutaneous by cannulating the MAC Pin 10 so that this procedure could be performed percutaneously. That way a percutaneous posterior instrumentation of the vertebral body could be performed in adjunct with an anterior lumber interbody fusion or in adjunct with a trans lateral interbody fusion. So that this procedure and this system 10 can be utilized with almost any spinal pathology, spondylolisthesis, isthmic spondylolisthesis, traumatic spondylolisthesis also scoliosis, whether it be idiopathic or a degenerative condition, and finally spinal trauma.

This system 10 also provides a different coupler 20MO that is called a medial offset of lateral offset coupler. In this particular coupler 20MO, the MAC Pin 10 would still be placed in the vertebral body 202, but the coupler 20MO would be placed not cranial and caudal but rather medial or lateral to the MAC Pin 10 and in that situation the holes 21 where the rod 100 adjoins to the coupler 20MO would now be parallel with the rod 100 so that it could be medial or lateral to the MAC Pin 10. And that would enable the surgeon to perform multiple spondylolisthesis reductions. For example, if you had a (L4 L5) as well as a (L5 S1) grade 1 or grade 2 spondylolisthesis, one could use the medial offset coupler 20MO with a MAC Pin 10 at every vertebral body with a MAC Pin 10 placed at L4, L5 and S1 and then one could place a medial coupler 20MO on each MAC Pin 10 and therefore one could perform independent distraction or compression between both motion segments and then also independent and accurate reduction of both the L4 body on L5 as well as the L5 body on S1 once again achieving complete and consistent accuracy. And that is the uniqueness this particular device 10.

The system 10 is designed to reduce spondylolisthesis whether it be grade 1, grade 2 or grade 3 according to the surgeon's desire to reduce the spine.

In practicing these procedures, it is preferable that the surgeons are triangulating the MAC Pins 10 into the vertebral body 201 so that when the vertebral body 201 is pulled back or reduced that the force that is pulling the vertebral body 201 back to alignment is not only axial pullout strength, but also an actual purchase of the vertebral body through triangulating the MAC Pins 10 or converging the MAC Pins 10 from the right and left side in a triangular fashion in the vertebral body 201 so a separate force is pulling back against the mass of vertebral body 201, not only axial pullout strength of the MAC Pin 10.

In describing how the triangulation of the MAC Pins 10 within a vertebral body 201 would work, consider for example if the surgeon is fixing a L4,5 degenerative spondylolisthesis that means that the L4 body is translated or listhesed out of proper alignment forward or anteriorly maybe 2 mm maybe 2 cm. He has to pull that L4 body back where it belongs in a direct line within the sagittal plane. That direct line must be consistently and accurately reproduced from surgery to surgery or else it could create rotation within the motion segment that will put a mechanical malalignment and possibly other problems. Every time he pulls back on spondylolisthesis an upper bone on top of a lower bone it must be in a symmetrical fashion and also along a vector directly within the sagittal plane. In order to do that, what is going to be done is to put a standard pedicle screw in the vertebral body below. The rod 100 is fixed within that pedicle screw 110 so that the pedicle screw 100, the rod 100, the vertebral body 202 are all fixed with respect to each other. This will serve as an anchor to pull back the L4 vertebral body within that sagittal plane. In order to establish a strong foothold in the upper vertebral body L4, the surgeon must do one thing and that is to insure a very strong purchase or grasp of that L4 vertebral body 201 and pull it back using the rod 100, pedicle screw 110 and vertebral body 202 below once again as an anchor. Once the coupler 20 is placed on the MAC Pin 10 and the surgeon begins to pull the vertebral body above 201, back within that sagittal plane, he must have achieved a strong foot hold and grasp of that L4 vertebral body 201. The preferred way he would do that is from the right side and left side. He would place the MAC Pins 10 in the upper vertebral body at angles. He would come in at as an obtuse or oblique angle with respect to the sagittal plane or the vector within the sagittal plane that the bone must pull back in. In the way he want the MAC Pins 10 not only with strong axial pullout strength, but also wants the two MAC Pins 10 coming in from both the right and left side at an angle, preferably anywhere between 15 and 25 degrees in a convergent way so that the tips of the MAC Pins 10 are coming together within the midline of the upper vertebral body 201. For example L4, once the MAC Pins 10 are hooked into the anchor at the rod 100 again to translate both right and left MAC Pins 10 with respect to the anchor or rod 100 the vertebral body 201, the vertebral body can be translated posteriorly into alignment symmetrically within the sagittal plane. The foothold that is achieved by doing this is twofold. One, the MAC Pin 10 itself has an axial pullout strength that is going to add to the foothold. Two, by angulating the two MAC Pins 10 in a convergent manner within the vertebral body 202 increases the foothold on the medial aspect of the each of the MAC Pins 10 purchasing the mass of the vertebral body 202, the mass of the bone also serves as a foothold for a grasp of the vertebral body 202 as the surgeon pulls the vertebral body 202 along a straight vector within the sagittal plane. It is because the angles of the MAC Pins 10 that are oblique to the sagittal plane, the force begins to pull within the vector of the sagittal plane. The obliqueness of the MAC Pin 10 has added strength for pulling the vertebral body back within that sagittal plane. Once that alignment is achieved, then the MAC Pins 10 are locked down and the actual pullout strength as well as the convergence of the two MAC Pins within the vertebral body 202 continue to hold that vertebral body within an aligned or reduced position until the fusion takes place.

This system 1 allows the surgeon to pull from left and right sides if desired. The MAC Pin in the right or the left side allows not only for independent distraction or compression right versus left according to the need, but they also allow complete independent rotational control so that a surgeon if he wanted to could pull the right MAC Pin 10 back 1.5 cm, pull the left MAC Pin only 1 cm to create rotation within the vertebral motion segment so that the spondylolisthesis or scoliosis can be tuned to the situation the surgeon is seeing. The benefit of this device 10 is that if he had a rotation that could place the vertebral out of alignment, the surgeon would be able to distinctly and independently rotate, distract or reduce the vertebral right versus the left independent of each other the right or the left sides. It all depends on the technique the surgeon uses whether he reduces by the handle on the right side or the left side or both simultaneously or he can, if he chooses, utilize the MAC Pin 10 and the handle the right side versus the left side differently at different times completely independent of one another.

There is nothing on the market that allows this reproducible, consistent accuracy with regard to distraction, rotation, and in particular reduction. The market has been flooded by multiple spinal instrumentation companies with what's called "reduction screws". Reduction screws are just standard pedicle screws that have a long extended tulip. They are based on the fact that you can try and lock the lower pedicle screw in the lower vertebral body and then estimate again estimate the amount of reduction, translation or rotation that one might need and then a reduction screw is placed in the vertebral body above. At this point the theory is the rod is again fixed to the vertebral body below and again in this system the vertebral body below and the pedicle screw and the rod are fixed together and are going to be used as an anchor while the tulip and the end cap is placed on the reduction screw above. So the theory is that as the screw end cap down into this elongated reduction tulip at the relationship between the upper vertebral body and the lower vertebral body are going to remain the same and that is just simply never true and never accurate and never reproducible.

As one begins to reduce the spondylolisthesis with a reduction screw, what happens is, the surgeon must rely on the anchor in the lower vertebral body 202, the standard pedicle screw 110 and the rod 100. And the theory is that he would like the rod 100 to be sitting the exact same distance in the tulip that he desires the spondylolisthesis to be reduced. So he is looking at an interoperative forum, so when the surgeon says he wants the reduce this spondylolisthesis let's say 5 mm, he is going to set the rod 5 mm above the bottom of the tulip on the reduction screw, then he is going to put the end cap in the reduction screw and tighten the end cap until the rod sits on the base of the tulip which will be 5 mm. The only problem with this system is that it requires that the pedicle screw and rod relationship in the vertebral body below does not change a bit. And that is where the problem with this system comes in is that it always changes. So what happens is the surgeon puts 5 mm between the rod and the tulip head and begins to tighten the end cap and what happens is that as the end cap tightens down the rod takes the vertebral body below into a different angulation and into a different position such that once you get to 5 mm of tightened down with the end cap, he may only have achieved 1-2 maybe 3 mm of reduction, and once that end cap is set within the tulip that is all he's got. So that means he wanted to reduce 5 mm, but the vertebral changed in its angle relationship, then he only had 3 mm, then he has to reset that and there is no way to change that unless he takes out the rod and starts over. That adds time to the patient's surgery and a surgeon may find himself readjusting this 2, 3 to 4 times trying to get the estimation correctly based on something he has no control over. This relationship is based on the strength of the bone, meaning that if the pedicle screw in the vertebral body below moves, if it toggles within the vertebral body then that is going to take away 2-3 mm or if the polyaxial head of the screw anchor in the lumber vertebral body below starts to move at all will take away 2-4 mm of reduction. And finally, if the relationship within the sagittal plane of the upper vertebral body and the lower vertebral body begin to change with the respect to one another as the end cap is tightened down assuming the rod, the pedicle screw and the lower vertebral body are indeed fixed, then what has happened is the two vertebral bodies move inappropriately with relationship to each other and then again a loss of 3, 4, 5 mm of reduction occurs and so what it's going to result in is making the surgeon accept mediocrity. While reducing a grade 2 spondylolisthesis, to 0 in perfect alignment is usually found with that type of prior art instrumentation is a grade is not completely reduced, not completely restored within that mechanical alignment in the sagittal plane. In the present invention system 1, the surgeon does not have to worry about those things. He won't have to even consider any of those things that cause problems with the reduction screw system, because the MAC Pin 10 allows adjustable, and reproducible amount of reduction or translation regardless of the relationship of the lower vertebral body 202, it has no bearing on the procedure other than being an anchor point. You can take it to 1-2 cm, if you want to you can take anterior again, so you have complete control forward and backwards moving this vertebral body anywhere in space you want to and that is within the interoperative amount of time which is so important that with the system 1 which takes less than 5 minutes to reproduce consistently, the device 10 allows free independent reduction and rotation of vertebral body 201 with an additional time of less than 5 minutes. And no one can argue that the reduction pedicle screws allow for that amount of control with that few minutes of interoperative time addition.

Figure 4C:
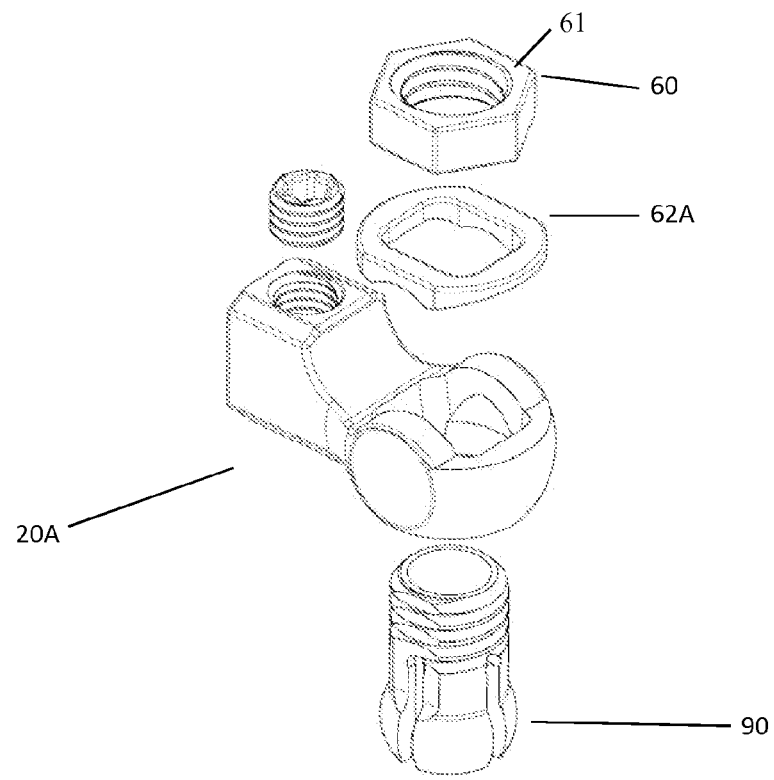
FIG. 4C shows an additional view of an alternative multi-axial or polyaxial coupler providing an ability to slightly tilt angle the MAC Pin in any direction to facilitate installation of the system.
Figure 4D:
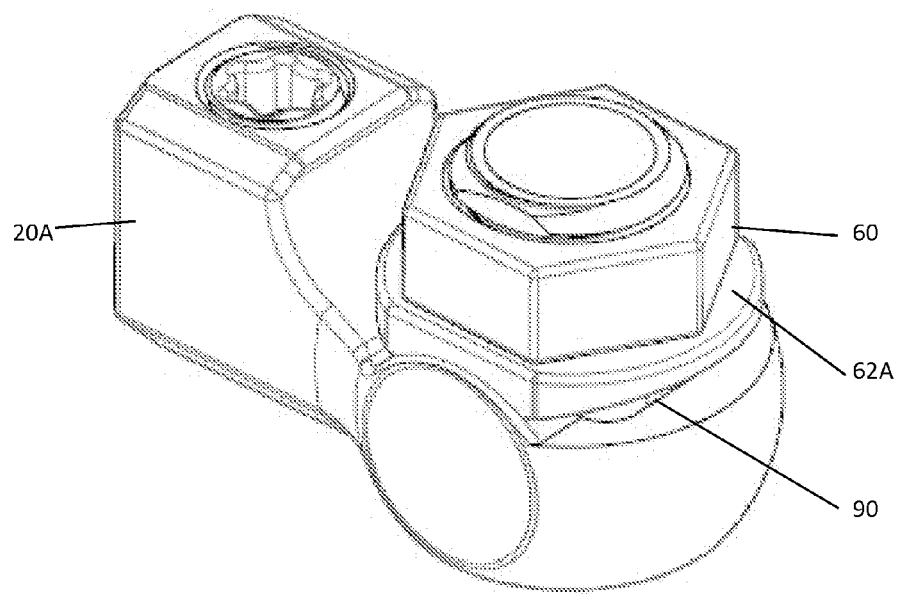
FIG. 4D is the alternative coupler of FIG. 4C shown in a perspective view assembled.
Figure 4E:
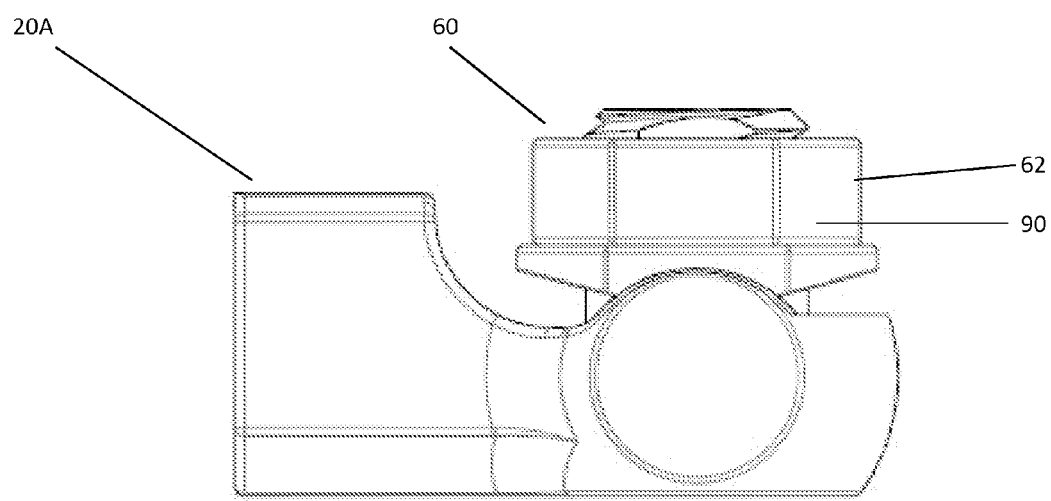
FIG. 4E is a side view of the coupler of 4D assembled.
Figure 4F:
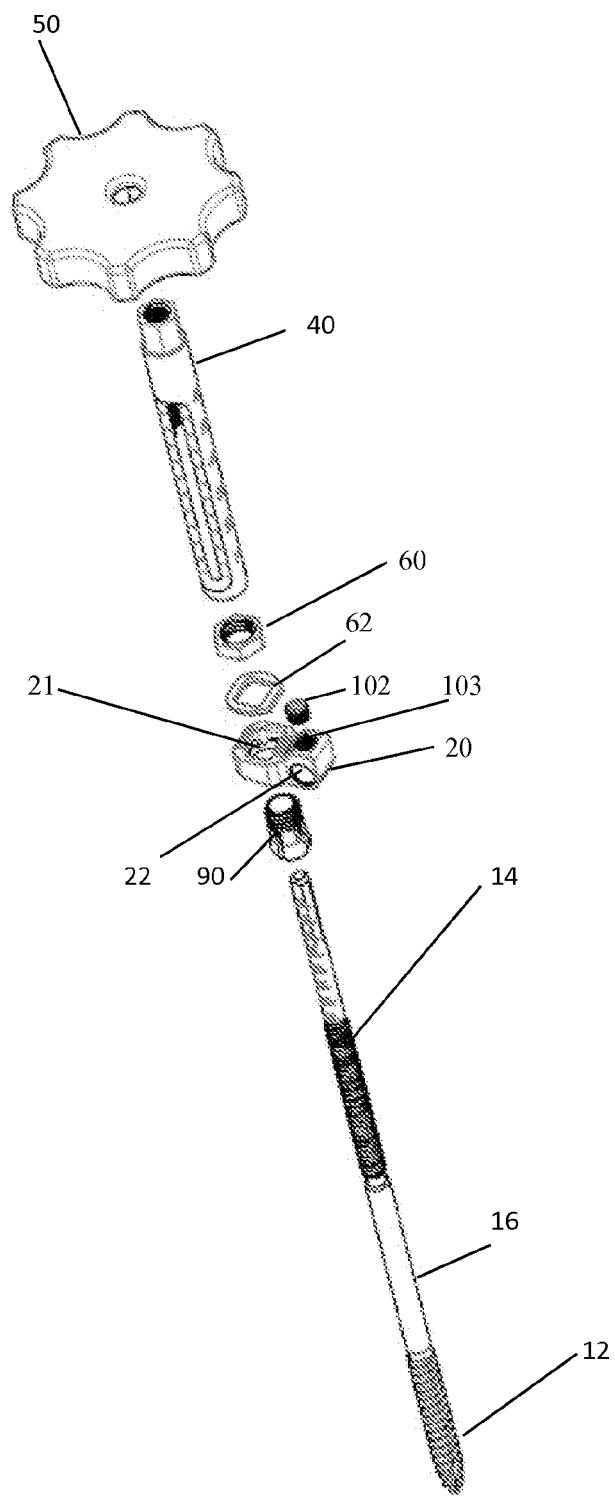
FIG. 4F is an alternative embodiment of the present invention shown in an exploded perspective view illustration of the MAC Pin made as a multi-piece posted lumbar pedicle screw and illustrating a medial offset or lateral offset coupler design.
Figure 4G:
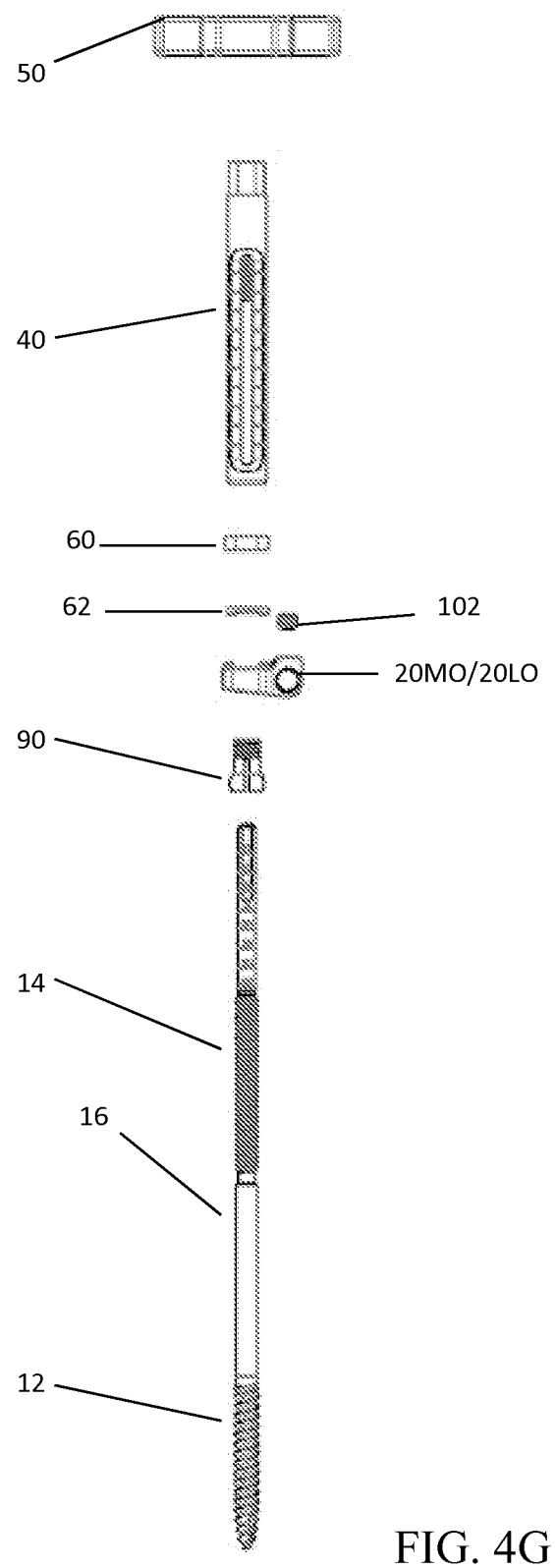
FIG. 4G is a side view of the alternative embodiment.
Figure 4H:
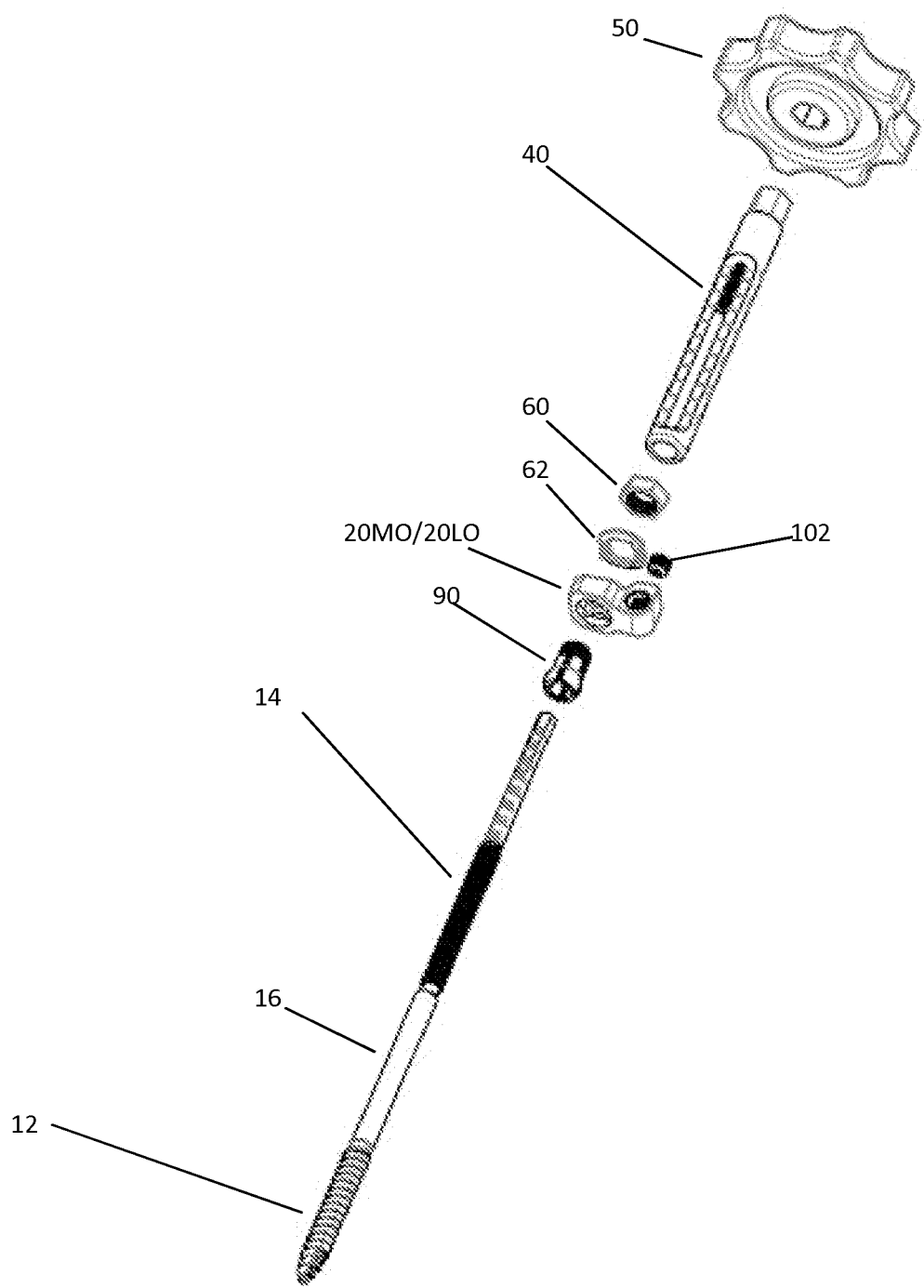
FIG. 4H is a perspective view.
Figure 4I:
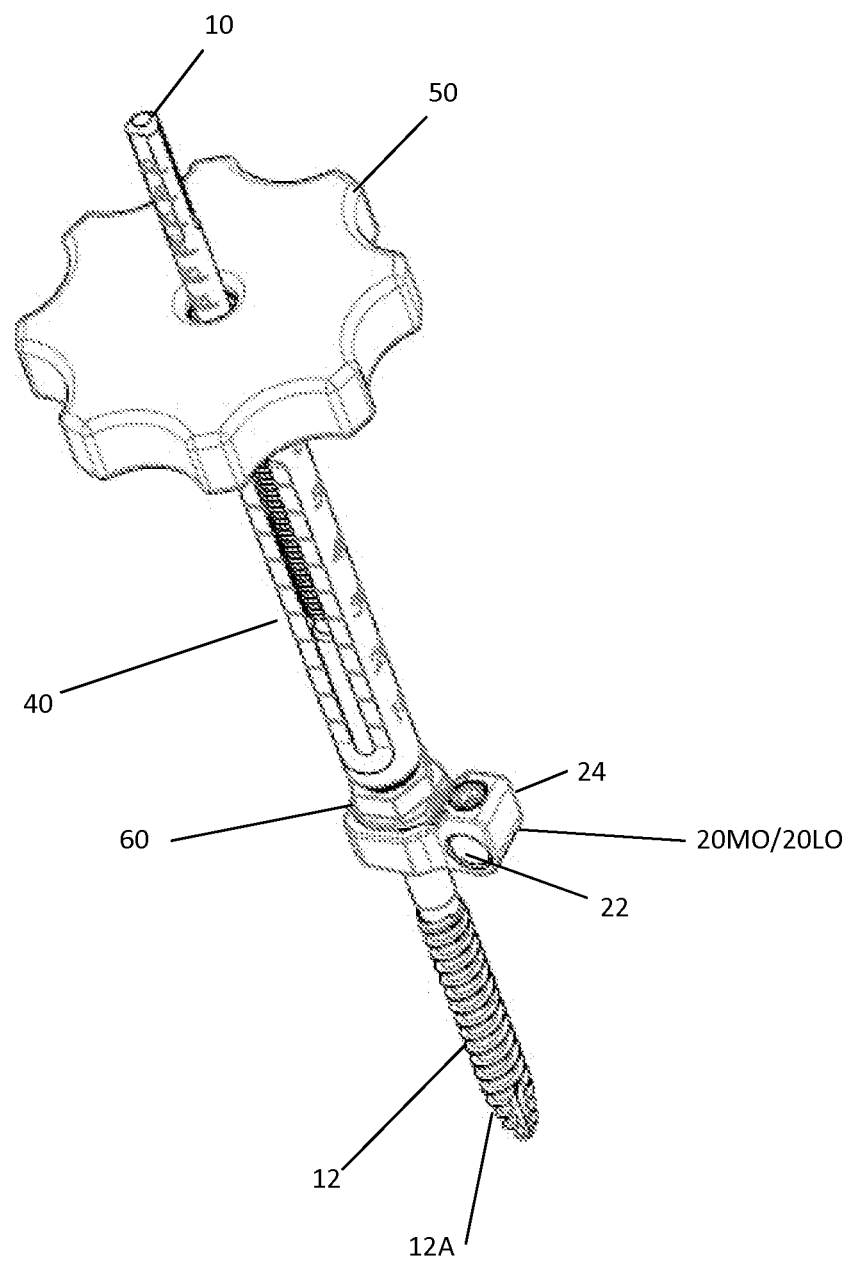
FIG. 4I is an assembled view.
Figure 10A:
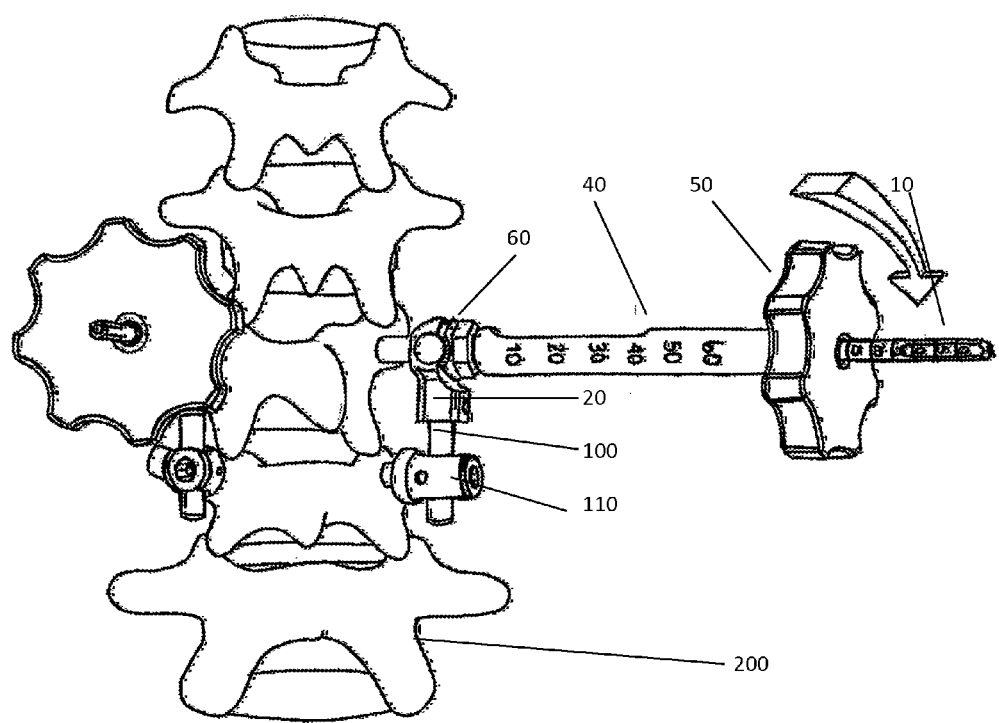
FIG. 10A shows a scoliosis treatment and how the system can be used to also provide a rotational correction of a vertebral body.
Figure 10B:
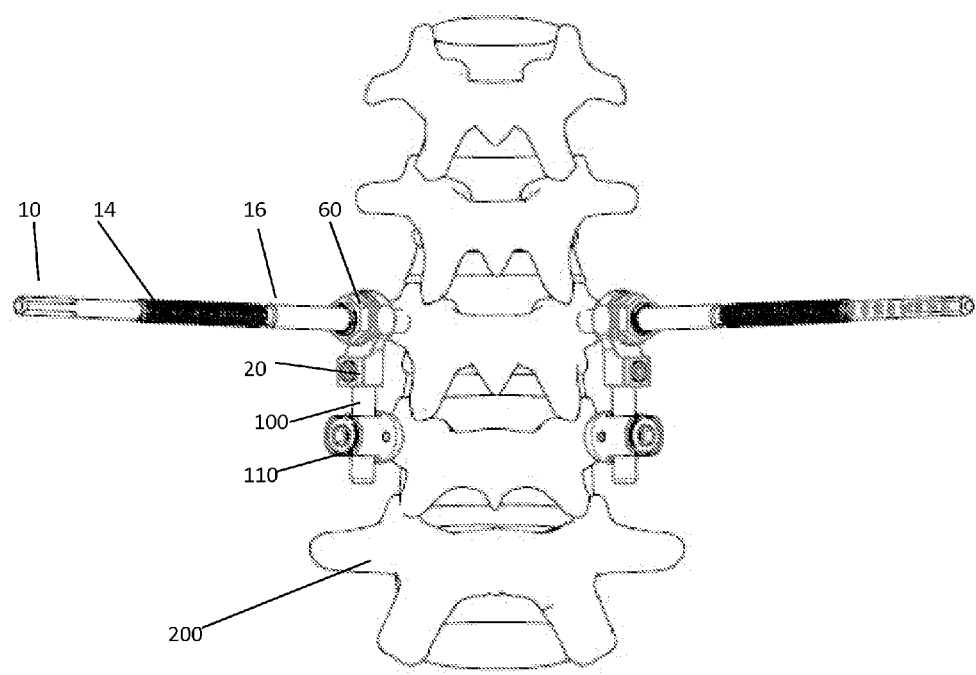
FIG. 10B is a view showing the correction result provided to the spine segment of FIG. 10A.
Figure 11:
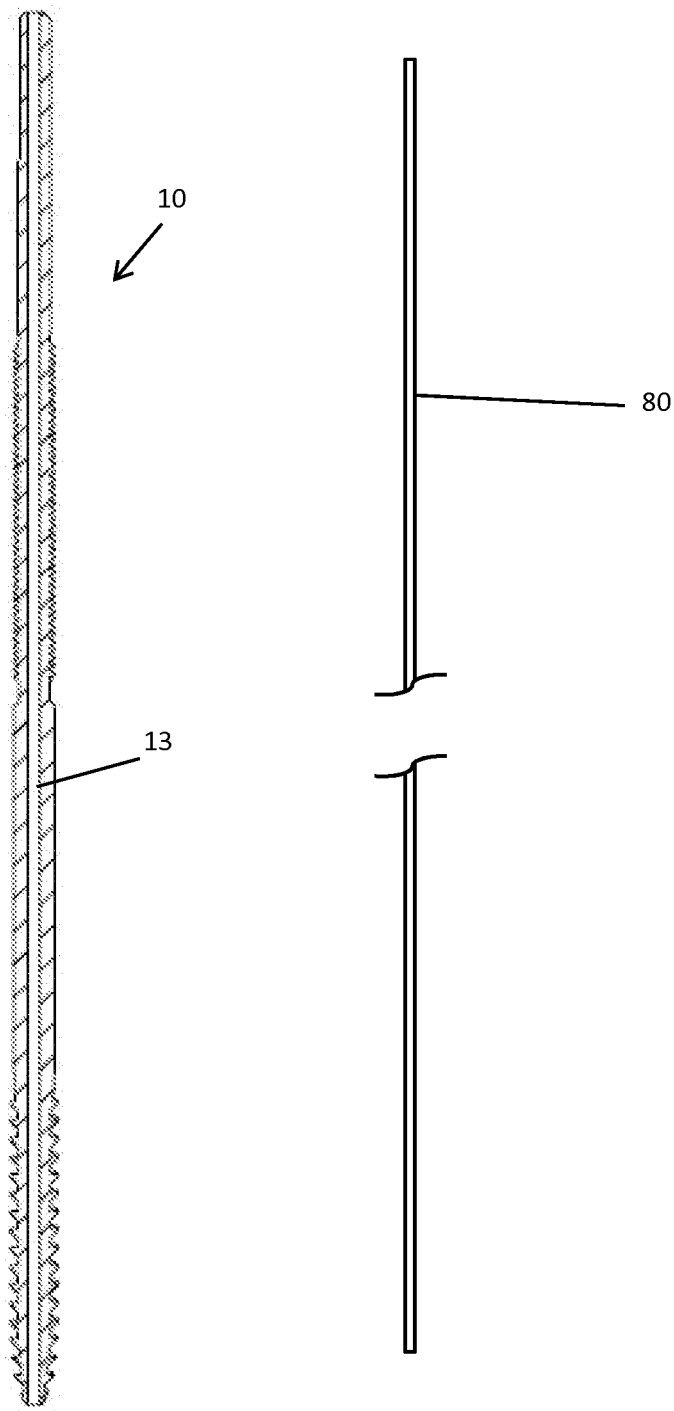
FIG. 11 is a view of a cannulated MAC Pin for use with a K-wire in a percutaneous procedure.

With regard to application of the system 1 in scoliosis, the MAC Pin 10 would be used and probably in every level of the scoliosis. As shown in FIGS. 10A and 10B, in a scoliotic spine 200 where a curve had to be reduced in the sagittal plane but also rotationally reduced, the MAC Pin 10 would be placed bilaterally, most likely, sometimes unilaterally in multiple levels throughout the entire affected instrumented spine. Every level that is going to be addressed with instrumentation in scoliosis may have one or two MAC Pins 10 in them. With regard to the coupler 20, in scoliosis, most likely the coupler 20 could be a medial offset coupler 20MO or a lateral offset coupler 20LO as opposed to the cranial coupler 20 that would be used in spondylolisthesis. In the coupler 20MO or 20LO, the rod connection opening is positioned on a side of the coupler body 24 as shown in FIGS. 4F-4I. In this alternative embodiment, the MAC Pin 10 is made as at least a two part assembly, the pedicle screw 12 and the smooth transition 16 and second threaded portion 14 are separate. Otherwise the alternative embodiment is similar in construction as the system 1 previously discussed. As designed one can use a coupler 20 as previously described in FIGS. 4-4B having monoaxial adjustment or a polyaxial construct as shown in FIGS. 4C-4E, or use a fixed coupler 20 design as illustrated for the couplers 20LO/20MO which by design are the same in terms of the location of the rod opening 22. This allows the use of multiple MAC Pins 10 within the spine 200 and then the rod 100 would be placed either medially or laterally through the MAC Pin 10 and then coupled to the MAC Pin 10 again from the medial side or the lateral side. The rod 100 would most likely be utilized bilaterally in both the right and the left side to add a foothold or strength to the purchase of the various vertebral bodies of the spine 200 for not only reduction in not only the sagittal and coronal plane again also rotational such that again the MAC Pin 10 on the right side of the vertebral body 201 versus the MAC Pin 10 on the left side of the vertebral body 201. Either way has complete independence from each other so that a surgeon may be able to utilize the MAC Pin 10 for rotation on the right side by leaving the left side in place. So the medial coupler 20MO purpose or lateral coupler 20LO simply would allow the MAC Pin 10 to be utilized in the vertebral body at multiple different levels. The MAC Pin 10 with regard to scoliosis procedures likely would be exactly the same, however, the coupler 20 going from what is called the cranial coupler to a medial or a lateral offset coupler, required the coupler design to be slightly different in the fact that the coupler 20 is slipped over the MAC Pin 10 and if for example the medial offset is placed on the MAC Pin 10, the rod 100 would be placed medial to the MAC Pin 10 so therefore the slot or the hole 21 within the coupler 20 would need to run parallel with the axis of the spine 200, such that the only difference would be that the coupler 20MO allows the rod to be medial to the MAC Pin 10 as opposed to being caudal to the MAC Pin 10. So the wrenches 70 that would be used would be the same, the two nuts 60 would be very similar, the only difference would be the relationship to the right of the MAC Pin and this is all based on the fact that the surgeon would need to place multiple MAC Pins 10 throughout the spine 200.

With regard to the physical structure of the MAC Pin 10, this will be a one piece titanium pin with two sets of threads, there will be a pedicle screw portion 12 that will measure anywhere from 35 to 55 mm and will replicate at this point a pedicle screw thread. That typically is a double lead pedicle screw self-tapping thread with the single pole. Alternatively, in future generations the thread can be with the double threaded dual core system for the pedicle portion of the MAC Pin 10. Beyond the inner tip 11A of the pedicle screw portion 12 of the MAC Pin 10 there will be a smooth shaft portion 16 that will be from 1 to 2 cm or 1 to 3 cm in length and will be the same dimensions or radius as the inner core or shaft of the MAC Pin 10 most likely of the pedicle screw portion and that will be the space that is allowed for coupling of the coupler 20 to come down over the MAC Pin 10. Furthermore beyond the smooth shaft portion 16 of the MAC Pin 10 there will be an outer portion 14 with a second set of threads. That second set of threads will be the threads that are actually used for the reduction or rotation of the vertebral body 201 by virtue of the fact that cannulated smooth shaft hitting a smooth surface of the coupler 20 over the MAC Pin 10 and this smooth cannulated tower has an inner set of threads that will operate and engage with the outer second set of threads on the outer portion 14 of the MAC Pin 10. When the cannulated handle goes over the tip 11B of the MAC Pin 10 and one rotates the outer cannulated tower 40 with respect to the MAC Pin 10 and because the coupler 20 is fixed to the rod 100 and vertebral body below, as you rotate the shaft 40 over the MAC Pin 10 that begins to pull the MAC Pin 10 in posteriorly within the sagittal plane and obviously the pedicle screw itself threaded within in the vertebral body 202 is going to pull the vertebral body back. So the final and last portion of the post or end of the MAC Pin 10 is simply again some type of squared off structure that will allow potentially a grasp of the MAC Pin so it can be rotated, if desired. The tip of the MAC Pin 10 may be smooth or squared off, it doesn't matter to the function of the MAC Pin because all of the function of the MAC Pin 10 takes place in the second set of threads within the cannulated tower 40. The MAC Pin 10 is a screw that can be used with an open procedure, but the same pin can be cannulated for the purpose of percutaneous reductions and percutaneous use. The coupler 20 is loose on the non-threaded smooth shaft transition portion 16. The transition portion 16 has no threads and has a smooth uniform or constant outer diameter extending along at least the majority of the length of the transition portion 16, preferably along the entire length of the transition portion 16, as shown in FIG. 3. The outer diameter of the transition portion 16 is at least equal to a maximum diameter of said second thread 14A. The coupler 20 that is on the MAC Pin 10 is loose on the smooth shaft portion of the MAC Pin and that relationship is not fixed. So although the tower between the outer diameter of the shaft pin and the inner diameter of the coupler is quite small it does allow the MAC Pin 10 to shift or cam within the coupler 20 so that as you are tightening down the cannulated tower 40, the MAC Pin 10 is actually shifting or moving with respect to the coupler 20 so that the vertebral body portion of the MAC Pin 10 is remaining fixed. So the MAC Pin 10 within the vertebral body does not move, it only pulls the vertebral body 201 back through the cam action between the cannulated tower 40 and the coupler 20 and the MAC Pin 10. That is why the MAC Pin 10 is made smooth on that one portion of the pin 10. As you are pulling the vertebral body 201 back you are rotating the cannulated tower 40 moving outwardly the MAC Pin so the inner threads within the shaft 40 are operating in conjunction with the outer threads of the MAC Pin 10 so that the both sets of threads are slowly driving the vertebral body back within the sagittal plane. The MAC Pin 10 moves fore or aft relation to the rotational direction of the shaft 40. Importantly, the MAC Pin 10 is not rotating as the cannulated tower 40 rotates and pushes against the coupler 20. The rod 100 has already been placed in the coupler 20, the rod 100 and the pedicle screw 110 below are the anchor. The MAC Pin 10 could spin within the coupler 20 at this point, but keep in mind the coupler 20 is fixed to the rod 100 which is fixed to the pedicle screw 110 below. The only motion that is remaining is the camming effect with respect to the MAC Pin 10 inside of the coupler 20. Once the cannulated tower 40 has reduced the spondylolisthesis to the desired amount the cannulated tower 40 stays in place, one takes the handle or cogwheel 50 off the top and a cannulated wrench 70 is placed over both the cannulated tower 40 and the MAC Pin 10 and goes all the way to the coupler 20 where there is a nut 60 to tighten. As the nut 60 tightens, the relationship between the coupler 20 and MAC Pin 10 becomes fixed. There are two nuts on the coupler 20, one nut 102 is in order to fix the coupler 20 to the rod 100, the other nut 60 is placed on the threaded end of the coupler 20 over the MAC Pin 10. So the nut compresses the coupler at the same hole that accommodates the MAC Pin 10, so when the coupler is all the way down on the bone one tighten the nut and it fixes the relationship between the MAC Pin 10 and the coupler 20. When one sends the cannulated tower 40 down the MAC Pin 10 the threads between those two entities are locked together that is what gave the reduction and so you leave that cannulated tower 40 on until one puts the wrench 70 over and tightens the nut 60. That fixes everything, it fixes the relationship between the coupler 20 and the MAC Pin 10, therefore locks in the reduction achieved with the vertebral body in place. The nut 60 is sitting there on the coupler 20 and doesn't get tightened until one tightens it with the cannulated wrench 70. The nut 60 as designed will slide over the cannulated tower 40 and onto the coupler 20 so the nut 60 is going to slide over the shaft 40 and tighten on that slotted thread end area on the coupler 20 and when that area on the coupler 20 gets tightened down it will tighten down on the smooth shaft portion 16 of the MAC Pin 10.

Interbody fusion is not necessary, but if desired after shearing off MAC Pin post. The only implant you would have would be an interbody implant.

After the instrumentation has been placed after the MAC Pin has been sheared off flush with the coupler, the reduction and the distraction or compression of the spondylolisthesis has been achieved and has been fixed with regard to the instrumentation. If a surgeon chooses at this point to decompress the neural elements or wishes to provide an interbody discectomy fusion or placement of an interbody posterior implant, now is the time that would be performed. At this point again after the instrumentation is complete with respect to the MAC Pin and the rod, a laminectomy or a laminotomy can be performed decompressing the neural elements. At this point a standard posterior lumber interbody fusion or a transforaminal lumbar interbody fusion can be performed. In which case the nerve root that has distracted from the midline and anulotomy is performed and the discwork including a total discectomy endplate preparation, insertion of bone graft material of choice and lastly insertion of a posterior interbody bone graft or cage dependent on surgeon's choice can be placed within the interbody space of the affected motion segment.

In that situation, the inventor has found that after distracting with the rod posteriorly that one can now place an interbody graft within the anterior column of the disc space and create a parallel distraction of the disc height and therefore restoring lordosis. At this point it is also available with this system once the interbody implant has been placed in the anterior column of the intervertebral disc space, it is now possible to leave the coupler and the MAC Pin fixed but if a surgeon wanted to compress on an interbody implant he would then simply go to the lower pedicle screw in the lower vertebral body, loosen the end cap and therefore enable them to compress on the rod thus, interbody implant and then retighten the end caps maintaining the listhesis but allowing once again independent distraction or compression.

With regard to placing the interbody implant, once the instrumentation is performed and the spondylolisthesis is reduced and locked in placed and fixed at that time a laminectomy or a laminotomy can be performed according to the surgeon's indication. At this point also would be a laminotomy and perhaps a posterior lumbar interbody fusion or a transforaminal interbody fusion. Also at that time the vertebral body may be retracted toward the midline and an anulotomy is made, and then finally a discectomy is performed in preparation and insertion of bone graft material according to the surgeon's choice. Once the bone graft has been placed in the interbody space, the surgeon then inserts the posterior interbody graft or cage according to his desire.

After the placement of the interbody structure the surgery would be complete. There is an option if the surgeon wants to create more lordosis, he has two different ways to do that. One would be to insert a large interbody graft anteriorly in the anterior column as one is opening up the anterior disc space creating parallel disc height distraction or even a lordotic alignment. The second method by which the surgeon could create lordosis with this system 1 is at this point once the interbody implant is placed in the anterior column. He can loosen the end caps in the lower vertebral body standard pedicle screw and then perform compression of the rod within the standard pedicle screws at which point he will therefore be compressing not only the interbody graft or cage but also creating a lordotic alignment within the motion segment that has been instrumented. Once that compression takes place, then the surgeon would simply tighten up the end caps in the pedicle screws below and then the entire concept would be rigid and fixed. All the while the spondylolisthesis by virtue of the MAC Pin 10 and the coupler 20 have been made fixed and therefore the spondylolisthesis does not change, this is a unique feature to the system 1. If a reduction pedicle screw on the lower pedicle screw is locked in the monoaxial position, and forms the anchor by which the reduction screw is going to be utilized using the prior art technique, the surgeon can then not go back and loosen this tulip head or else the reduction would be lost if the reduction screw had changed. This unique system 1 allows that feature which is again another benefit to accuracy and reproducible consistency of the system. The system with regard to rotational control as well as reduction control within that part of the spine. At this point the surgery would be complete and the surgeon would then begin his standard closure.

One of the other features that is unique within the coupler 20 is that the MAC Pin 10 relationship within the coupler 20 not only has a cam relationship that can shift within the coupler 20 up and down, but it also will be able to change angulation with respect to the coupler 20. That is the MAC Pin 10 will be able to change the angulation with regard to the coupler within the sagittal plane. There is a shaft holding coupling mechanism 90 within the coupler 20, a separate shaft holding coupling mechanism 90, within the titanium coupler 20 that moves with relationship to the coupler 20 itself, so as the MAC Pin 10 comes down through the coupler 20 it is also coming through this separate device 90 so that this coupling 90 allows movement within the sagittal plane with respect to the coupler and the importance of that is to allow MAC Pin 10 to enter into the pedicle at the vertebral body at different angles cranial or caudal within the sagittal plane. So that when the coupler 20 and the rod 100 are introduced simultaneously over the MAC Pin 10, if there is an odd or unexpected angle in order for the caudal aspect of the rod 100 to fall into the top loading tulip of the pedicle screw 110, this motion within the coupler 20 will accommodate that need. Such that when the coupler 20 is placed over the MAC Pin 10, and the rod 100 needs to fall down into the space of the tulip head of the pedicle screw 110 below that shaft holding coupling mechanism 90 within the coupler 20 and that motion would then apply to the frame to allow that accommodation to occur. A side to side motion with respect to the device 90 inside the coupler 20 also can be provided to match the couple relationship. That purpose will be to allow surgeons a larger margin of error with regard to the angle at which he places his MAC Pin 10 into the vertebral body. So the system 1 allows for a margin of error respecting the fact that not all surgeons are going to optimally position the device 10 every time. The device 10 automatically can compensate for this fact. The placement of pedicle screws has long been known to be a skill that is developed and learned by each individual spine surgeon. So it was desirable to want to remove as much requirement for the perfect placement of this MAC Pin within the vertebral body as possible, therefore allowing the largest margin of error for surgeons to place the MAC Pin and then connect it through a rod, pedicle screw below. This device within the coupler currently has the ability to move within the sagittal plane both cranial and caudally allows for that and allows the coupler 20 to be attached to the rod 100 in the pedicle screws. Preferably, the coupler 20 is designed with 360 degree motion so as to allow the surgeon margin of error not only in the sagittal plane but also within the coronal plane such that regardless of the surgeons ability to place the MAC Pin 10 appropriately within the vertebral body, the attachment into the rod 100 and the pedicle screw 110 below would be made even easier for that surgeon.

In another embodiment, the device or system 1 provides a percutaneous MAC Pin. The MAC Pin 10 design would be the same; however, it is cannulated inside the entire length pin such that this could be done with a minimally invasive procedure as opposed to an open procedure. That would decrease the patient's postoperative pain, decrease the blood loss, decrease the hospital stay length, as well as decrease the patient's long term postoperative pain. Another benefit of doing this procedure percutaneously is that one could then couple this procedure with an anterior lumbar interbody fusion or perhaps a translateral interbody fusion and use a separate approach while placing these pins and reduce the spondylolisthesis percutaneously or in a minimally invasive technique.

With regard to the coupler 20, the coupler 20 probably would not change although modification improvements of the coupler 20 are certainly possible. The most important part of the procedures would remain the same the MAC Pin and the fact that under fluoroscopic assistance interoperatively a stab wound in the skin would be made as opposed to a complete opening of the skin and muscle tissue. So a small k wire (kirschner wire) could be inserted into the pedicle and finally into the vertebral body maintaining the above described technique and that would be followed by the placement of MAC Pins that would be cannulated and then attached to the coupler and the pedicle screw below. Similarly described in the open procedure. A jamsheedy needle would be used to place the guide wire into the vertebral body again percutaneously or minimally invasive and this is certainly a standard well known part of the procedure. However, once the guide wire 80 had been placed and confirmed to be in the appropriate placement, per the interoperative fluoroscope and that would be followed by measuring of the pedicle screw portion of the MAC Pin and then placement of the MAC Pin 10 with a cannulated opening 13 over the guide wire 80 and into the vertebral body to appropriate position based on the interoperative fluoroscope.

Figure 12A:
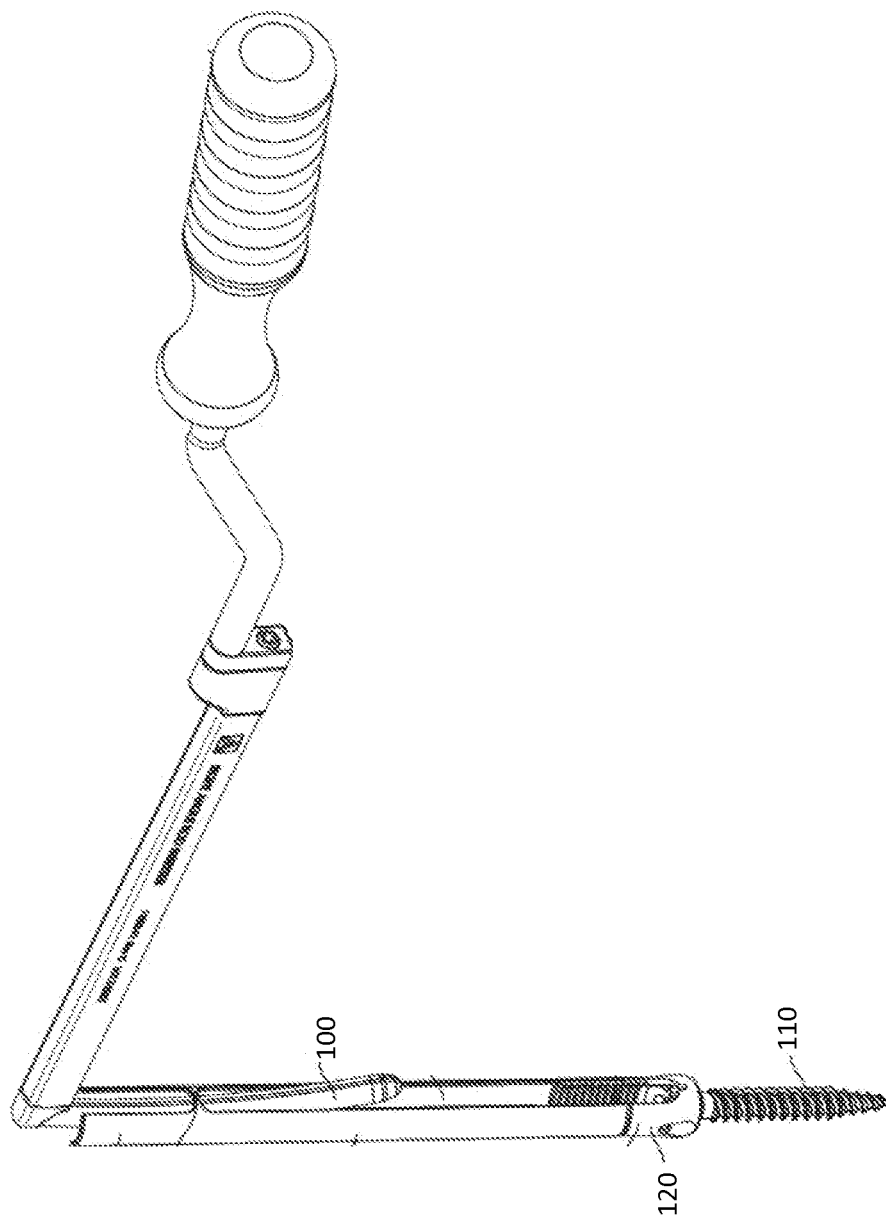
FIG. 12A is a perspective view of an insertion tool, inserting a stabilizer rod into a bone screw system with leg extensions for use in a percutaneous procedure.
Figure 12B:
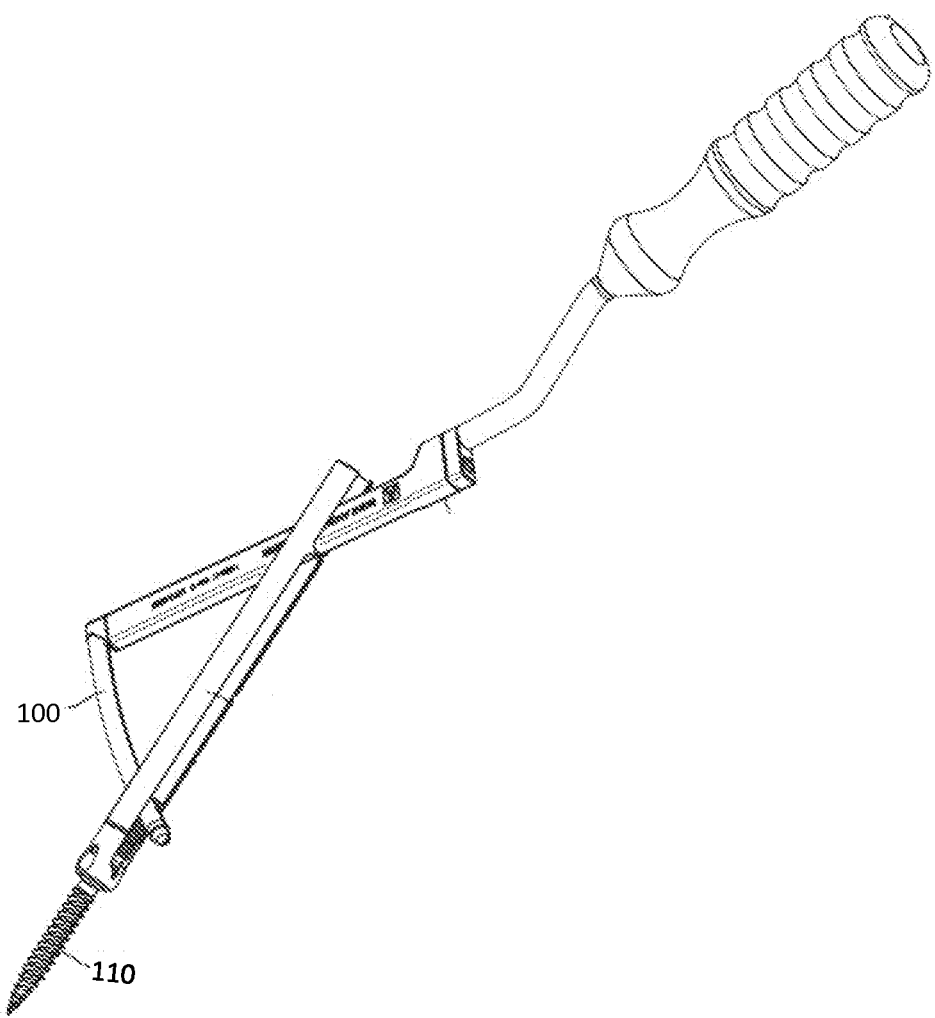
FIG. 12B is a perspective view of the insertion tool of FIG. 12A, showing the insertion tool using the connector as a fulcrum to maneuver the stabilizer rod into position.
Figure 12C:
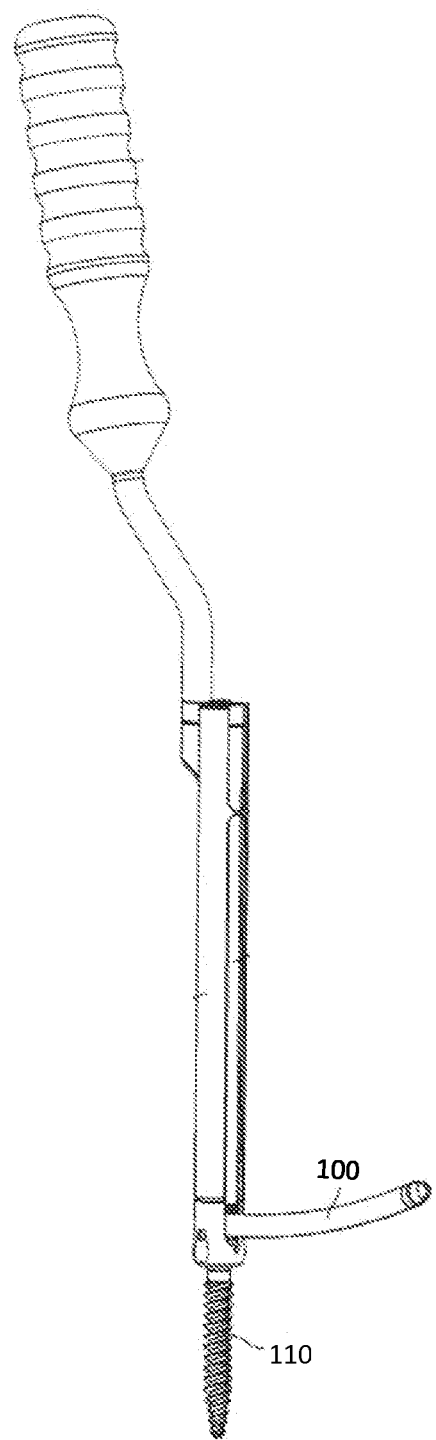
FIG. 12C is a perspective view of the insertion tool of FIG. 12A, showing the insertion too using the connector as a fulcrum to further maneuver the stabilizer rod into position.

The next step would be placement of percutaneous pedicle screws, shown in FIGS. 12A-12C, in the previously described placement of percutaneous pedicle screws already established by the assignee of this system as described in co-pending US patent publication 2013/0172937 A1 entitled "Extended Tab bone Screw System" filed Dec. 19, 2012; which is incorporated by reference herein in its entirety; and finally the coupler 20 would be applied over the MAC Pins 10 as described in the open technique and placed within the tulip head below through a minimally invasive being separately described. In another aspect, the two leg extensions are connected via a connector 249 positioned at a point spaced therefrom the first end of the leg extension and spanning the first insertion tool pathway 270. In one aspect, the connector is positioned substantially perpendicular to the longitudinal axis AL. Positioning the connector 249 a predetermined distance from the first end provides a fulcrum point from which a rod insertion tool can rotate. As seen in FIGS. 19, 20 and 21, the stabilizer rod is positioned between the leg extensions with the insertion tool. As the stabilizer rod is positioned lower and toward the second end of the leg extensions, the insertion tool is partially positioned between the leg extensions. At this point, the handle of the insertion tool can be lifted, using the connector as a fulcrum to push the stabilizer rod into position within the rod receiving channel. At that point once again, the end caps on the pedicle screws below would be tightened and fixed once again to serve as an anchor for the MAC Pin after which the surgeon would go back to the MAC Pin 10 and begin the translation and distraction procedure as described above such that after reduction was achieved through the action of the MAC Pin, the cannulated wrench would be slipped over and the nut would once again be tightened and a separate shearing device would be developed to shear the MAC Pin flush with the coupler. And once again the surgeon has achieved a fixed reduced spondylolisthesis that he can now go and perform either anterior lumbar interbody fusion, lateral and foraminal interbody fusion or a posterior lumbar interbody fusion and perhaps even "OLIF" at this point consistent with amendia's portfolio.

Variations in the present invention are possible in light of the description of it provided herein. While certain representative embodiments and details have been shown for the purpose of illustrating the subject invention, it will be apparent to those skilled in this art that various changes and modifications can be made therein without departing from the scope of the subject invention. It is, therefore, to be understood that changes can be made in the particular embodiments described, which will be within the full intended scope of the invention as defined by the following appended claims.

What is claimed is:

1. A maximum alignment correction pin comprising:
an elongated shaft having an overall length from an inner leading tip end to an outer or distal end of at least 100 mm, the elongated shaft having a pedicle screw thread portion, a second thread portion and a transition portion;
the pedicle screw thread portion having or adjacent the inner leading tip end of the shaft and having pedicle screw threads extending along the shaft a distance of at least 40 mm for fastening the shaft into vertebral bone;
the second thread portion disposed toward the outer or distal end of said elongated shaft, said second thread portion having a second thread configured to engage a cannulated tower having complimentary threads which when rotated allow for moving a vertebrae along a sagittal plane to alignment;
the transition portion on said elongated shaft spaced between the pedicle screw thread portion and the second thread portion, wherein the transition portion has a smooth uniform or constant outer diameter extending in length along the transition portion from 1 to 3 cm, the outer diameter of the transition portion being at least equal to a maximum diameter of said second thread,
the transition portion configured to receive an untightened rod coupler loosely connected and movable to slide freely within the transition portion, the loosely connected rod coupler having a rod affixed for connection to a tulip of an embedded pedicle screw; and
wherein the elongated shaft has the pedicle screw thread portion configured to be embedded in the vertebrae and once the pedicle screw thread is embedded, the elongated shaft with the pedicle screw portion does not rotate, but moves longitudinally as the second threads are moved by rotation of the cannulated tower abutted against the untightened rod coupler with the rod affixed loosely sliding along the length of the smooth transition moving the vertebrae to alignment where the coupler is then tightened against the transition portion of the maximum alignment correction pin and the transition portion of the elongated shaft cut flush to the coupler removing the second thread portion.

2. The maximum alignment correction pin of claim 1 wherein the pedicle screw thread portion includes a self-tapping tip end feature for bone entry at or adjacent the inner leading tip end.

3. The maximum alignment correction pin of claim 1 wherein the pedicle screw thread is a double thread pedicle screw thread.

4. The maximum alignment correction pin of claim 1 wherein the pedicle screw threads extend between 50 to 55 mm up the length of the shaft.

5. The maximum alignment correction pin of claim 1 wherein the pedicle screw thread portion is a double threaded post lumbar pedicle screw.

6. The maximum alignment correction pin of claim 5 wherein the distal end has one or more flat surfaces to facilitate rotation of the elongated shaft.

7. A spinal alignment correction system comprising:
an elongated shaft having an overall length from an inner leading tip end to an outer or distal end of at least 100 mm, the elongated shaft having an inner pedicle screw thread portion with pedicle threads, an outer second thread portion with second threads and a transition or intermediate portion disposed between the pedicle screw thread portion and the outer second thread portion, the inner pedicle screw thread portion having or adjacent the inner leading tip end of the shaft and extending along the shaft a distance of at least 40 mm for fastening the shaft into vertebral bone, the outer second thread portion disposed toward the outer or distal end of said elongated shaft, said outer second thread portion having the second threads configured to engage a cannulated tower having complimentary threads which, when rotated about said second threads, allow for moving a vertebrae along a sagittal plane to alignment, wherein the transition portion has a smooth uniform or constant outer diameter extending in length along the transition portion from 1 to 3 cm, the outer diameter of the transition portion being at least equal to a maximum diameter of said second thread;
a rod coupler assembly having a coupler body which has a pair of openings, a first opening for passing over the elongated shaft and being movable lengthwise to slide freely within the transition or intermediate portion and a second opening for receiving a rod; and
wherein the elongated shaft has the pedicle screw thread portion configured to be embedded in the vertebrae and once the pedicle screw thread is embedded, the elongated shaft with the pedicle screw portion does not rotate, but moves longitudinally as the second threads are moved by rotation of the cannulated tower abutted against the untightened rod coupler assembly with the rod affixed loosely sliding along the length of the smooth transition moving the vertebrae to alignment where the rod coupler assembly is then tightened against the transition portion of the maximum alignment correction pin and the transition portion of the elongated shaft cut flush to the rod coupler assembly removing the outer second thread portion.

8. The spinal alignment correction system of claim 7 wherein the rod coupler assembly is rotationally movable about said shaft.

9. The spinal alignment correction system of claim 7 further comprising:
a cannulated tower, the cannulated tower having a longitudinally extending opening having internal threads complimentary to said second thread of said elongated shaft; and
wherein the cannulated tower, when mounted over said elongated shaft, abuts said rod coupler assembly along an outer cam surface of a nut which is included in said rod coupler assembly and further tightening rotation of the cannulated tower causes outward elongated shaft movement.

10. The spinal alignment correction system of claim 9 further comprising:
a handle removably attached to the cannulated tower to facilitate rotation of the cannulated tower.

11. The spinal alignment correction system of claim 10 further comprising:
a first rod fastener, said first rod fastener when attached to said threaded opening in the coupler body locks a rod securely fixed in the second opening for receiving the rod.

12. The spinal alignment correction system of claim 11 further comprising:
a washer; and
wherein the nut included in said rod coupler assembly is for attachment onto the coupler body to abuttingly lock said washer against said coupler body.

13. The spinal alignment correction system of claim 12 further comprising:
a rod, the rod having a first end and a second end;
a second rod fastener;
a pedicle screw with rod receiving connection; and
wherein said pedicle screw when affixed to a lower vertebral body has the rod extend to the second rod receiving opening of the rod coupler assembly positioned over the elongated shaft affixed to an upper vertebral body, when the first end of the rod is placed in said rod receiving connection of the pedicle screw and fixed by said second rod fastener, the second end of the rod is placed in the second opening of said coupler body and fixed to said coupler body by the first rod fastener after a desired vertebral alignment is achieved.

14. The spinal alignment correction system of claim 7 wherein the elongated shaft is made of titanium.

* * * * *